US012569296B2

(12) United States Patent
Primeaux

(10) Patent No.: US 12,569,296 B2
(45) Date of Patent: Mar. 10, 2026

(54) LEFT-ATRIUM-TO-CORONARY-SINUS SHUNT

(71) Applicant: Medtronic Vascular, Inc., Santa Rosa, CA (US)

(72) Inventor: Jonathan Primeaux, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 735 days.

(21) Appl. No.: 17/820,689

(22) Filed: Aug. 18, 2022

(65) Prior Publication Data

US 2023/0099410 A1 Mar. 30, 2023

Related U.S. Application Data

(60) Provisional application No. 63/249,963, filed on Sep. 29, 2021.

(51) Int. Cl.
A61B 18/14 (2006.01)
A61B 18/00 (2006.01)

(52) U.S. Cl.
CPC .. A61B 18/1492 (2013.01); *A61B 2018/0016* (2013.01); *A61B 2018/00214* (2013.01);
(Continued)

(58) Field of Classification Search
CPC ........ A61B 18/1492; A61B 2018/0016; A61B 2018/00214; A61B 2018/00351; A61B 2018/00577
See application file for complete search history.

(56) References Cited

U.S. PATENT DOCUMENTS 9,138,230 B1 * 9/2015 Buelna ................... A61B 18/18
9,439,710 B2 9/2016 Reu et al.
(Continued)

FOREIGN PATENT DOCUMENTS

WO 2019109013 A1 6/2019
WO 2020215090 A1 10/2020
(Continued)

OTHER PUBLICATIONS

Extended Search Report from counterpart European Application No. 22195598.2 dated Feb. 7, 2023, 10 pp.
(Continued)

*Primary Examiner* — Linda C Dvorak
*Assistant Examiner* — Abigail Bock
(74) *Attorney, Agent, or Firm* — Shumaker & Sieffert, P.A.

(57) ABSTRACT

An ablation system, configured to create a shunt between a left atrium and a coronary sinus of a patient, includes an ablation device comprising a proximal body defining a distal-facing surface configured to contact the coronary sinus wall, a distal body defining a proximal-facing surface positioned opposite the distal-facing surface and configured to contact the left atrium wall, and first and second heating elements disposed on the distal-facing and proximal-facing surfaces, respectively. The heating elements are configured to ablate tissue between the left atrium and the coronary sinus of the patient to create the shunt. The system further includes an expandable dilation element configured to dilate a puncture formed through the coronary sinus wall and the left atrium wall to facilitate introduction of the distal body of the ablation device into the left atrium.

26 Claims, 23 Drawing Sheets

(52) U.S. Cl.
CPC .............. *A61B 2018/00351* (2013.01); *A61B*
*2018/00577* (2013.01)

(56) References Cited

U.S. PATENT DOCUMENTS

| | | | | |
|---|---|---|---|---|
| 9,757,194 | B2 | 9/2017 | Werneth et al. | |
| 2004/0073238 | A1 | 4/2004 | Makower | |
| 2004/0158143 | A1* | 8/2004 | Flaherty ........... | A61B 17/12109 |
| | | | | 600/407 |
| 2011/0257723 | A1 | 10/2011 | McNamara | |
| 2012/0259263 | A1* | 10/2012 | Celermajer .... | A61B 17/320016 |
| | | | | 604/509 |
| 2014/0163652 | A1 | 6/2014 | Witzel et al. | |
| 2014/0228843 | A1 | 8/2014 | O'Donnell et al. | |
| 2016/0270845 | A1 | 9/2016 | Benscoter et al. | |
| 2018/0193084 | A1 | 7/2018 | Sklar et al. | |
| 2020/0000511 | A1 | 1/2020 | Morejohn et al. | |
| 2020/0178968 | A1* | 6/2020 | Foerster ............... | A61B 18/082 |
| 2020/0229875 | A1 | 7/2020 | Keast et al. | |
| 2020/0289196 | A1 | 9/2020 | Arevalos et al. | |
| 2021/0007790 | A1 | 1/2021 | Takahashi et al. | |
| 2021/0077186 | A1 | 3/2021 | Pate et al. | |
| 2021/0177508 | A1 | 6/2021 | Kellerman et al. | |

FOREIGN PATENT DOCUMENTS

| | | |
|---|---|---|
| WO | 2020219265 A1 | 10/2020 |
| WO | 2021091566 A1 | 5/2021 |

OTHER PUBLICATIONS

Medtronic, "Ellipsys Vascular Access System, Transform Your AV Fistula Creation," Brochure, downloaded on Jun. 10, 2021, 3 pp.

"Ellipsys Transforming AV fistula creation," accessed on Jun. 10, 2021 from https://avenumedical.com/ellipsys/, 2 pp.

Chauvin et al., "The Anatomic Basis of Connections Between the Coronary Sinus Musculature and the Left Atrium in Humans", Circulation, vol. 101, No. 6, Feb. 15, 2000, 6 pages.

Shah et al., "Imaging of the Coronary Sinus: Normal Anatomy and Congenital Abnormalities", RadioGraphics, vol. 32, No. 4, Jul.-Aug. 2012, 20 pages.

Simard et al., "Levoatrial to Coronary Sinus Shunting as a Novel Strategy for Symptomatic Heart Failure: First-in-Human Experience", Journal of the American College of Cardiology, vol. 74, No. 13, Sep. 2019, 1 pp.

Communication pursuant to Article 94(3) EPC from counterpart European Application No. 22195598.2 dated May 13, 2025, 7 pp.

* cited by examiner

| Proximal Body Size (D) (Fr) | Proximal Body Size (D) (mm) | Electrode Length (L) (mm) | Shunt Area (mm²) |
|---|---|---|---|
| 9 | 3.0 | 6.0 | 14.1 |
| 10 | 3.3 | 6.7 | 17.5 |
| 11 | 3.7 | 7.3 | 21.1 |
| 12 | 4.0 | 8.0 | 25.1 |
| 13 | 4.3 | 8.7 | 29.5 |
| 14 | 4.7 | 9.3 | 34.2 |
| 15 | 5.0 | 10.0 | 39.3 |

180 — ADVANCE GUIDEWIRE

182 — ADVANCE DELIVERY SHEATH

184 — EXPAND POSITIONING ELEMENT

186 — ADVANCE PUNCTURING TOOL

188 — EXPAND DILATION ELEMENT

190 — ADVANCE ABLATION DEVICE

192 — RETRACT PROXIMAL BODY

194 — ADVANCE PROXIMAL BODY OR RETRACT DISTAL BODY

196 — ACTUATE HEATING ELEMENT(S)

198 — WITHDRAW MEDICAL SYSTEM

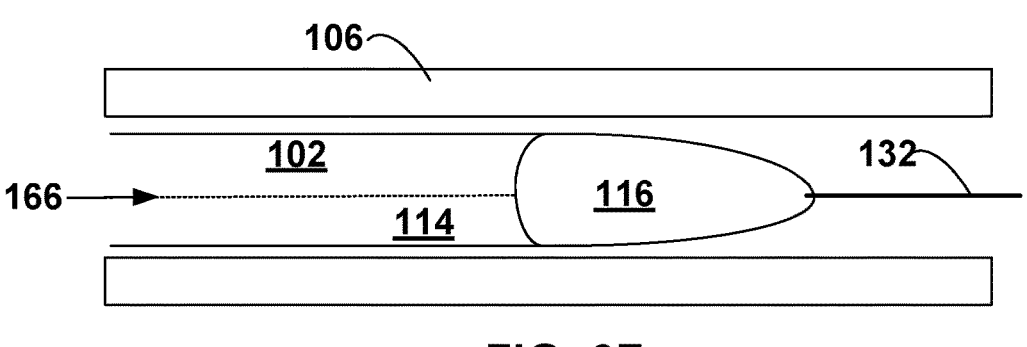
FIG. 6F
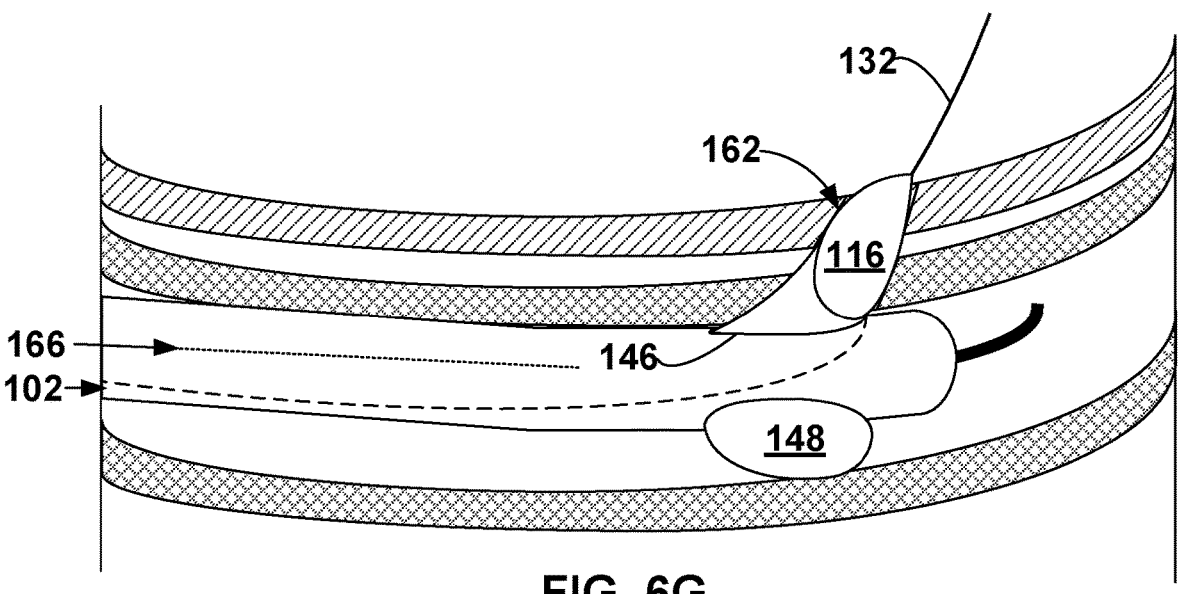
FIG. 6G
FIG. 6H

LEFT-ATRIUM-TO-CORONARY-SINUS SHUNT

This application claims the benefit of U.S. Provisional Application No. 63/249,963, filed Sep. 29, 2021, and entitled, "LEFT-ATRIUM-TO-CORONARY-SINUS SHUNT," the entire content of which is incorporated herein by reference.

TECHNICAL FIELD

This disclosure generally relates to medical devices.

BACKGROUND

Pulmonary edema (or "oedema") is an excessive build-up of fluid in the lungs of a patient. Pulmonary edema may result from one or more conditions, including heart failure. A heart of a patient with heart failure may not efficiently pump blood, which may cause a pressure build-up within the blood vessels and may cause fluid to be pushed into the lungs. Patients experiencing a pulmonary edema currently have limited treatment options.

SUMMARY

The present disclosure describes systems, devices, and techniques for creating a fluid pathway, or shunt, between the left atrium of a heart of a patient and the coronary sinus of the patient. The shunt can be used to, for example, treat pulmonary edema. In examples described herein, a medical system includes a dilation element configured to dilate an initial puncture through a target treatment site, and an ablation device configured to extend through the dilated puncture and form the shunt at the target treatment site. The ablation device includes a proximal body defining a distal-facing surface, and a distal body defining a proximal-facing surface positioned opposite the distal-facing surface of the proximal body. A first heating assembly, comprising a first heating element, is disposed on the distal-facing surface, and a second heating assembly, comprising a second heating element, is disposed on the proximal-facing surface. The proximal and distal bodies are axially movable relative to each other, such that sections of tissue, e.g., a portion of the coronary sinus wall and the left atrium wall, may be compressed or "sandwiched" between the distal-facing surface and the proximal-facing surface. The first and second heating elements are configured to heat to ablate the sections of tissue to create the shunt.

In some examples, the proximal and distal-facing surfaces are oriented at an oblique angle relative to a longitudinal axis of the device, such as an angle of about 15-90 degrees, for instance, about 15-50 degrees, relative to the longitudinal axis. The orientation of the proximal-facing surface parallels the orientation of the distal-facing surface, so that the proximal-facing and distal-facing surfaces are parallel and configured to fully engage with one another when actuated. The ablation device further includes an elongated structure (e.g., a shaft) that connects the distal body to the proximal body. The elongated structure is extendable and retractable to extend and retract the distal body relative to the proximal body.

In one example, a method includes: creating a puncture through a coronary sinus wall of a coronary sinus of a patient and a left atrium wall of a left atrium of a heart of the patient; expanding a dilation element within the puncture to dilate the puncture, resulting in a dilated puncture; advancing a distal body of an ablation device through the dilated puncture and into the left atrium, wherein the ablation device comprises: an elongated structure; a proximal body coupled to the elongated structure, the proximal body defining a distal-facing surface configured to contact the coronary sinus wall surrounding the dilated puncture; the distal body coupled to the elongated structure, wherein the proximal body and the distal body are longitudinally translatable relative to each other, the distal body defining a proximal-facing surface positioned opposite the distal-facing surface and configured to contact the left atrium wall surrounding the dilated puncture; a first heating element disposed on the distal-facing surface; and a second heating element disposed on the proximal-facing surface. The method further includes axially translating at least one of the proximal body or the distal body to compress the coronary sinus wall and the left atrium wall between the first heating element and the second heating element; and actuating the first and second heating elements to ablate the tissue to create a shunt between the left atrium and the coronary sinus.

In another example, a medical system includes an ablation device configured to create a shunt between a left atrium of a heart of a patient and a coronary sinus of the patient, the ablation device comprising: an elongated structure; a proximal body coupled to the elongated structure, the proximal body defining a distal-facing surface configured to contact a coronary sinus wall of the coronary sinus; a distal body coupled to the elongated structure and longitudinally translatable relative to the proximal body, the distal body defining a proximal-facing surface positioned opposite the distal-facing surface and configured to contact a left atrium wall of the left atrium; a first heating element disposed on the distal-facing surface; and a second heating element disposed on the proximal-facing surface, wherein the first and second heating elements are configured to ablate tissue between the left atrium and the coronary sinus of the patient to create the shunt; and a dilation element configured to expand to dilate a puncture formed through the coronary sinus wall and the left atrium wall to facilitate introduction of the distal body of the ablation device into the left atrium.

In some examples, a medical system includes an ablation device configured to create a shunt between a first anatomical structure and a second anatomical structure of a patient, the ablation device comprising: an elongated structure; a proximal body coupled to the elongated structure, the proximal body defining a distal-facing surface configured to contact a first wall of the first anatomical structure; a distal body coupled to the elongated structure and longitudinally translatable relative to the proximal body, the distal body defining a proximal-facing surface positioned opposite the distal-facing surface and configured to contact a second wall of the second anatomical structure; a first heating element disposed on the distal-facing surface; and a second heating element disposed on the proximal-facing surface, wherein the first and second heating elements are configured to ablate tissues of the first wall and the second wall to create the shunt; a puncturing tool configured to form a puncture through the first and second walls; and an expandable balloon configured to expand to dilate the puncture to facilitate introduction of the distal body of the ablation device into the second anatomical structure.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 6A-6L are conceptual diagrams illustrating the technique of FIG. 5.

DETAILED DESCRIPTION

Figure 1:
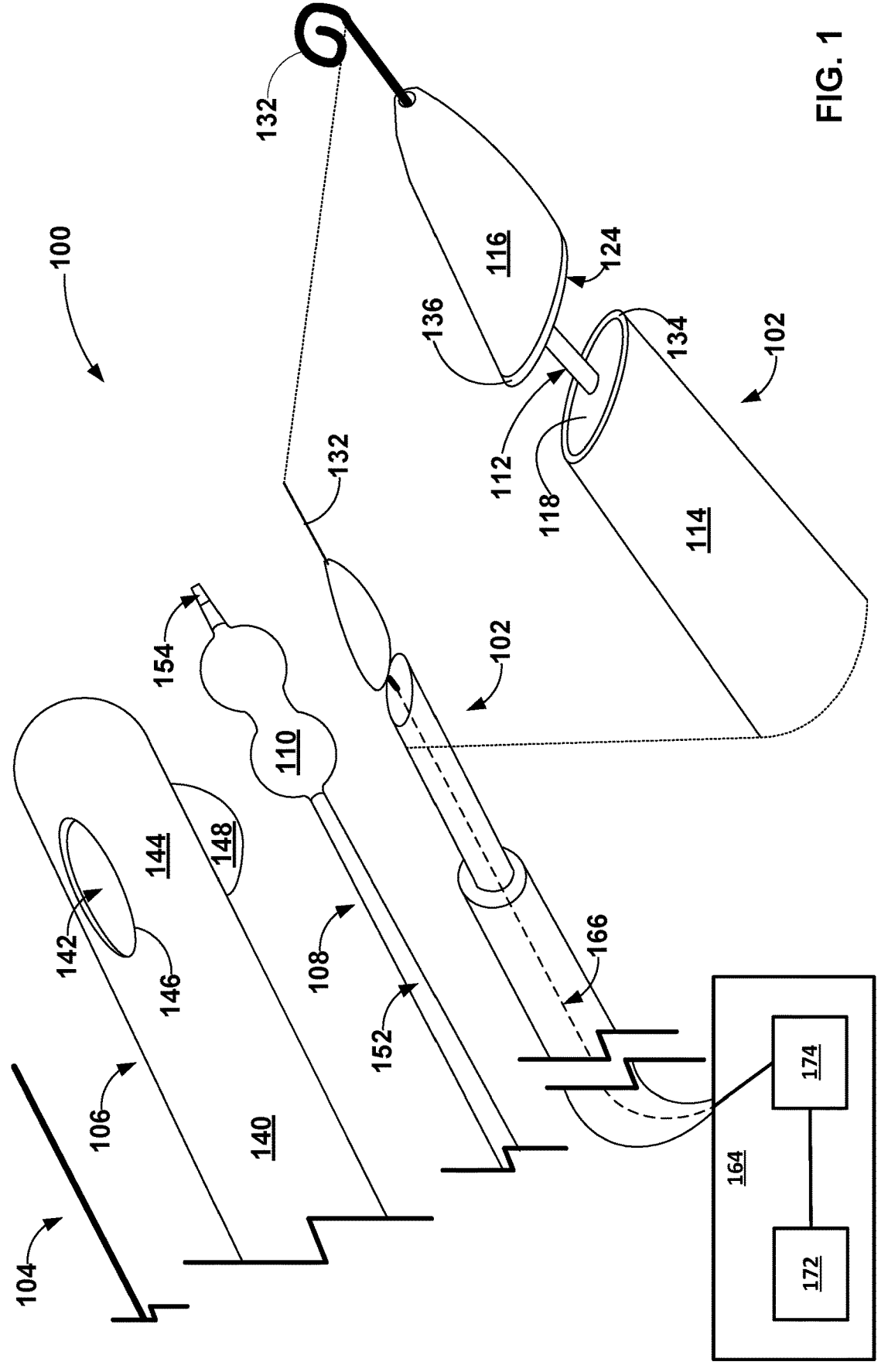
FIG. 1 is a perspective view depicting an example medical system, including an ablation device and a dilation element.

The disclosure describes examples of medical systems, devices, and techniques for creating a fluid pathway, or shunt, between a left atrium of a heart of a patient and a coronary sinus of the patient by at least delivering energy (e.g., radiofrequency (RF) energy) to ablate and fuse tissue of the left atrium and the coronary sinus together. Due to the nature of the ablation, the tissue adjacent to the ablation will coagulate and define a fused opening between the left atrium and the coronary sinus, enabling pressure from the left atrium to decompress into the coronary sinus. This may help treat pulmonary edema, such as by mitigating a mechanism of pulmonary edema. In other examples, the systems, devices, and techniques described herein can be used to create a shunt between two other hollow anatomical structures of a patient and to treat other patient conditions. Thus, while a shunt between a left atrium of a heart of a patient and a coronary sinus of the patient is primarily referred to herein, the systems, devices, and techniques can be used for other medical procedures in other examples.

In examples described herein, a medical system includes a dilation element configured to dilate an initial puncture through a left atrium wall and a coronary sinus wall, and an ablation device configured to form the shunt at the initial puncture site. For instance, the dilation element may be configured to dilate the initial puncture to enable at least part of the ablation device to extend through the puncture into the left atrium from the coronary sinus. The dilation include can be, for example, part of the ablation device or coupled to a separate puncturing tool of the medical system. In some such examples, the puncturing tool includes an electrifiable distal tip configured to form the initial puncture.

The ablation device includes a proximal body defining a distal-facing surface, and a distal body defining a proximal-facing surface positioned opposite the distal-facing surface of the proximal body. A first heating assembly, comprising a first heating element, is disposed on the distal-facing surface, and a second heating assembly, comprising a second heating element, is disposed on the proximal-facing surface. As used herein, a "heating assembly" is a component of the ablation device that includes an "active" heating element (e.g., an electrifiable RF electrode, or the like), a "passive" heating element (e.g., a thermally conductive surface configured to redistribute heat received from an active heating element), or an integrated combination of such active and passive heating elements. The proximal and distal bodies are axially movable relative to each other, such that sections of tissue, e.g., a portion of the coronary sinus wall and the left atrium wall, may be compressed or "sandwiched" between the distal-facing surface and the proximal-facing surface. The first and second heating elements are configured to heat and subsequently ablate the sections of tissue to create the shunt.

The orientation of the proximal-facing surface parallels the orientation of the distal-facing surface, so that the proximal-facing and distal-facing surfaces parallel one another and fully engage with one another when actuated. In some examples, the proximal-facing and distal-facing surfaces are oriented at an oblique angle relative to a longitudinal axis of the device, such as an angle of about 15-90 degrees, for instance, about 15-50 degrees relative to the longitudinal axis. In some examples, the distal-facing surface of the proximal body is oriented at an angle of about 23 degrees relative to the longitudinal axis of the ablation device. This oblique angle increases the surface area of the proximal-facing and distal-facing ablation surfaces, enabling the formation of a relatively larger shunt despite space constraints, e.g., that may limit delivery of relatively large devices to the target treatment site.

The ablation device includes an elongated structure (e.g., a shaft) that connects the distal body to the proximal body, the elongated structure being extendable and retractable to extend and retract the distal body relative to the proximal body. In some examples, a temperature sensor is disposed near the first and/or second energized heating elements for providing closed-loop temperature control to the respective heating assembly.

The distal body comprises an outer surface, extending axially from the proximal-facing surface toward a distal-most tip, which defines an opening to an inner lumen of the distal body. The inner lumen is configured to receive a guidewire. For example, a maximum cross-sectional dimension (e.g., diameter) of the opening can be about the same size as a maximum cross-sectional dimension (e.g., diameter) of the guidewire, wherein the cross-sections are measured perpendicular to a longitudinal axis of the ablation device.

In some examples, the heating elements each include separate elliptical elements that are each configured to provide independent power delivery for heating and cutting. The separate elliptical elements can include an outer element and an inner element, the outer element being configured to deliver reduced heat to promote controlled desiccation and adhesion within a "weld zone" without cutting through tissue, e.g., to bond the coronary sinus wall to the left atrium wall around the perimeter of the ablated tissue. The inner element is configured to deliver increased heat to promote rapid cutting through tissue in a cutting zone.

Each of the first and second heating assemblies, and in some examples, the elongated structure, may include non-stick surfaces, e.g., either formed from or coated with a low-friction material. For instance, the non-stick surfaces have a surface finish defining an average roughness (Ra) of less than about 16 Ra. In some examples, a position sensor is provided for monitoring movement of the distal body relative to the proximal body.

The techniques of this disclosure can be used to treat pulmonary edema. For instance, forming a shunt between the left atrium and the coronary sinus (also referred to herein as a LA-CS shunt) with the systems and devices described herein enable the relief of fluid build-up in the lungs of a patient without requiring the permanent implantation of a foreign object (e.g., a stent or the like), leading to better patient outcomes. In addition, the systems and devices described herein are highly user-friendly, e.g., do not require extensive training for the clinician.

FIG. 1 is a perspective view depicting an example medical system 100 configured to form a shunt at a target treatment site (illustrated in FIG. 2) between a left atrium of a heart of a patient and the patient's coronary sinus. In the example shown in FIG. 1, medical system 100 includes ablation device 102 and a dilation element 110. In some examples, but not all examples, medical system 100 also includes a separate puncturing tool 108 including dilation element 110. In other examples, dilation element 110 can be part of ablation device 102 or a different device. Medical system 100 is also shown in FIG. 1 as including a guidewire 104, a delivery sheath 106, and an RF generator 164.

In the example shown in FIG. 1, ablation device 102 includes an elongated structure 112, a proximal body 114, and a distal body 116. In some examples, elongated structure 112 defines a device inner lumen configured to receive, e.g., a guidewire 104 and/or puncturing tool 108. Guidewire 104 can, for example, be used to help navigate ablation device 102 through vasculature of a patient to a target treatment site within the patient. Proximal body 114 is coupled to the elongated structure 112, and defines a distal-facing surface 118. Distal-facing surface 118 is configured to contact an interior surface of a coronary sinus wall 120 (FIG. 2) of a coronary sinus 122 of a patient. As detailed further below with respect to FIG. 3, in some examples, distal-facing surface 118 is oriented at an oblique (e.g., acute, as opposed to perpendicular) angle θ relative to the longitudinal axis 166 defined by elongated structure 112. This angle θ results in distal-facing surface 118 defining an oval or elliptical shape having a relatively greater surface area (as compared to the substantially circular cross-sectional area of proximal body 114, wherein the cross-section is taken directly perpendicular to longitudinal axis 166), and accordingly, a larger shunt aperture formed by ablation device 102.

Distal body 116 is coupled to elongated structure 112 and defines a proximal-facing surface 124. Proximal-facing surface 124 is positioned opposite distal-facing surface 118, and is configured to contact an interior surface of a left atrium wall 126 (FIG. 2) of a left atrium 128 of a heart 130 of the patient. In some examples, as detailed further below, one or both of proximal body 114 and distal body 116 are configured to be longitudinally translatable along a longitudinal axis 166 defined by elongated structure 112 to bring distal-facing surface 118 and proximal-facing surface 124 closer or further from each other. Thus, while an example in which distal body 116 is longitudinally translatable relative to proximal body 114 is primarily referred to herein, in other examples, proximal body 114 is longitudinally translatable relative to distal body 116 alone or in combination with distal body 116 being longitudinally translatable relative to proximal body 114. That is, proximal body 114, distal body 116, or both proximal body 114 and distal body 116 may be moved to bring distal-facing surface 118 and proximal-facing surface 124 closer to each other or further from each other. In addition, proximal-facing surface 124 of distal body 116 is angled so as to parallel distal-facing surface 118 of proximal body 114, such that, when mutually engaged via longitudinal translation, more than 50% (e.g., from about 90% to about 100%) of each of distal-facing surface 118 and proximal-facing surface 124 will be in physical contact.

In some examples, distal body 116 includes an atraumatic distal tip or distal portion, e.g., formed from a relatively soft polymer material. In some examples, a distal guidewire 132, such as a Nitinol wire or another elongated guide member, extends distally outward from a distal-most end of distal body 116. Guidewire 132 can be, for example, embedded in distal body 116 or extend through a lumen defined by distal body 116 and extend distally outward from a distal mouth of distal body 116. In some examples, guidewire 132, in addition to, or instead of, puncturing tool 108, is configured to function as a puncturing element configured to puncture through tissue of a patient to enable advancement of at least distal body 116 through the tissue.

A proximal (or "first") active heating element 134 is disposed on the distal-facing surface 118 of proximal body 114. In some examples, but not all examples, ablation device 102 includes a distal (or "second") active heating element 136 disposed on the proximal-facing surface 124 of distal body 116. Distal heating element 136 may be substantially similar to proximal heating element 134. For instance, each of proximal and distal heating elements 134, 136 may include a radiofrequency (RF) electrode configured to receive RF energy from RF generator 164 in order to heat to ablate tissues of the coronary sinus wall 120 and the left atrium wall 126 while these tissues are compressed between distal-facing surface 118 and proximal-facing surface 124. The heat applied to the tissues denatures and ablates the sandwiched tissues, as well as welds the periphery of the sandwiched tissues, thereby forming a shunt 138 (FIG. 2), or fluid pathway, between the coronary sinus 122 and the left atrium 128.

Additionally or alternatively to receiving direct RF energy from RF generator 164, proximal and/or distal heating elements 134, 136 can be heated using electrodynamic inductive energy. For instance, a primary heating coil can be integrated into proximal heating element 134, and a secondary heating coil, which can be tuned to the same natural frequency as the primary heating coil, can be embedded in distal heating element 136. As proximal heating element 134 heats via received RF energy, an electrical current passes through the primary coil, creating a magnetic field which acts on the secondary coil embedded in distal heating element 136, inducing another electrical current that heats the resistive element.

Delivery sheath 106 is configured to facilitate delivery of ablation device 102 to a target treatment site in a patient. Delivery sheath 106 includes an elongated tubular body 140 defining a sheath inner lumen 142. As shown in FIG. 1, an exterior surface of a side wall 144 of tubular body 140 defines a side opening 146 to sheath inner lumen 142.

Figure 2:
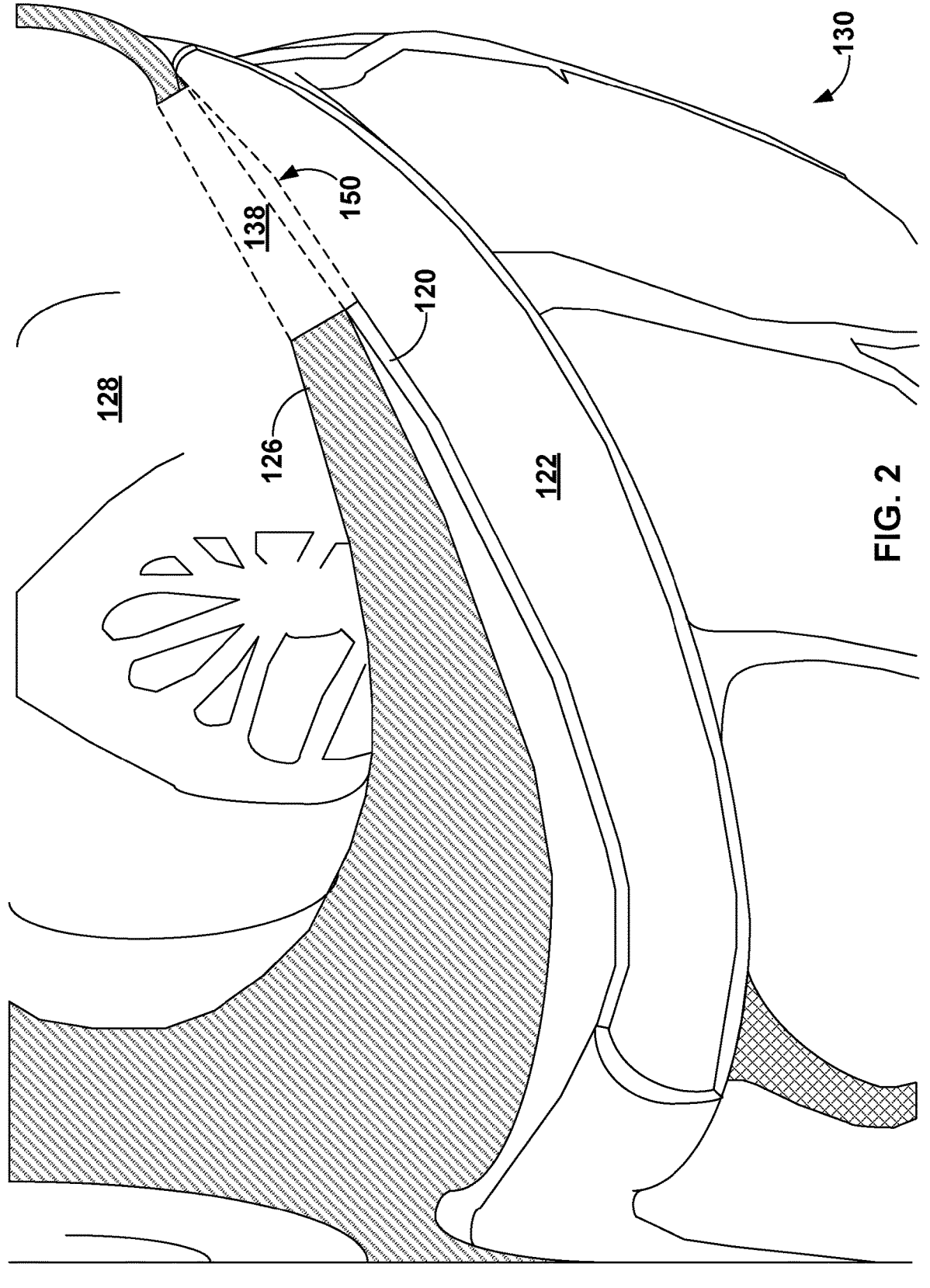
FIG. 2 is a cross-sectional view of an example heart of a patient, illustrating an example target treatment site between the left atrium and the coronary sinus. The cross-section is taken from an anatomical transverse plane through the heart, with FIG. 2 facing in a caudal direction toward the patient's feet.

In the example shown in FIG. 1, delivery sheath 106 further includes a positioning element 148, which is configured to help position opening 146 at a target treatment site. The location of opening 146 relative to tissue may define where an initial puncture is formed and/or where ablation device 102 forms shunt 138 (FIG. 2). Positioning element 148 is, for example, configured to engage with one part of a vessel wall (e.g., a coronary sinus wall 120, shown in FIG. 2) to bring opening 146 closer to another part of the vessel wall. For example, positioning element 148 may be located on side wall 144 at a position that is generally circumferentially opposite from side opening 146. For instance, positioning element 148 may be located about 150 degrees to about 210 degrees around the circumference of delivery sheath 106 from side opening 146, such as about 180 degrees. In these examples, positioning element 148 is configured to expand radially outward against the coronary sinus wall 120 in order to help position side opening 146 against a target treatment site 150 (FIG. 2) at a location on the coronary sinus wall 120 that is circumferentially opposite from the location on the coronary sinus wall 120 that contacts the positioning element 148.

Medical system 100 includes a puncturing element configured to form an initial puncture through coronary sinus wall 120 and left atrium wall 126. For example, the puncturing element can have an incisive tip configured to cut a pathway through tissue of a patient and/or another type of tip configured to define the pathway through tissue. In some examples, but not all examples, the puncturing element includes a distinct puncturing tool 108, which is physically separate from ablation device 102. In other examples, the puncturing element may be part of ablation device 102, such as the distal guidewire 132 (e.g., a Nitinol flat wire) extending from an atraumatic distal tip of distal body 116 of ablation device 102.

As shown in FIG. 1, puncturing tool 108 includes an elongated structure 152, such as a guidewire, a hypotube, a catheter body, or the like, and an electrifiable distal tip 154, which is configured to electrically heat to facilitate the forming of a puncture through coronary sinus wall 120 and left atrium wall 126. For instance, the electrifiable distal tip 154 may include a plasma electrode. In other examples, distal tip 154 is a relative sharp incisive tip facilitating puncture through purely mechanical means.

As detailed further below with respect to FIG. 4, in some examples, puncturing tool 108 further includes a dilation element 110, which is configured to expand radially outward to expand a puncture formed by puncturing tool 108. For instance, after distal tip 154 forms an initial puncture through each of coronary sinus wall 120 and left atrium wall 126, dilation element 110 may be at least partially advanced through the puncture and expanded radially outward to dilate the puncture (forming a dilated puncture). The dilated puncture facilitates subsequent advancement of distal body 116 of ablation device 102 into the left atrium 128 of the patient's heart 130 (FIG. 2). For example, the initial puncture formed by distal tip 154 may not be large enough to enable distal body 116 of ablation device 102 to extend through the puncture and into left atrium 128 of the patient from coronary sinus 122.

RF generator 164 includes control circuitry 172 and RF generation circuitry 174. In general, control circuitry 172 is configured to cause RF generation circuitry 174 to generate RF energy (e.g., monopolar and/or bipolar RF energy), and deliver the generated RF energy to proximal and/or distal active heating elements 134, 136. As described throughout this disclosure, control circuitry 172 may be configured to control, monitor, supply, and/or otherwise support operations of ablation device 102 and RF generator 164, e.g., by determining and implementing parameters (e.g., magnitude, frequency, etc.) of RF energy for delivery to tissue at the target treatment site via system 100.

Control circuitry 172 can have any suitable configuration. In some examples, control circuitry 172 includes any of a microprocessor, integrated circuitry, discrete logic circuitry, analog circuitry, such as one or more microprocessors, digital signal processors (DSPs), application specific integrated circuits (ASICs), or field-programmable gate arrays (FPGAs). In some examples, control circuitry 172 may include multiple components, such as any combination of one or more microprocessors, one or more DSPs, one or more ASICs, or one or more FPGAs, as well as other discrete or integrated logic circuitry, and/or analog circuitry.

Although not shown in FIG. 1, RF generator 164 can also include memory that stores instructions that are executable by processing circuitry 116. When executed by control circuitry 172, such instructions may cause control circuitry 172 to provide the functionality ascribed to control circuitry 172 herein. The instructions may be embodied in software and/or firmware. The memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

FIG. 2 depicts a cross-sectional view through a heart 130 of a patient, wherein the cross-section is taken with an anatomical transverse plane and viewed in a caudal direction (e.g., a direction away from the patient's brain and toward the patient's feet). In particular, FIG. 2 illustrates an example target treatment site 150 for forming a shunt 138 between the left atrium 128 of the heart 130 and the coronary sinus 122. In the example shown in FIG. 1, target treatment 150 site is located where coronary sinus wall 120 contacts, or is relatively proximate to, left atrium wall 126. This treatment site 150 may be accessed, in some examples, from a right jugular vein of the patient. Accordingly, in some examples, dimensions of ablation device 102 (FIG. 1) are specifically configured to accommodate a route through the patient's vasculature from the right jugular vein to the target treatment site.

Figure 3:
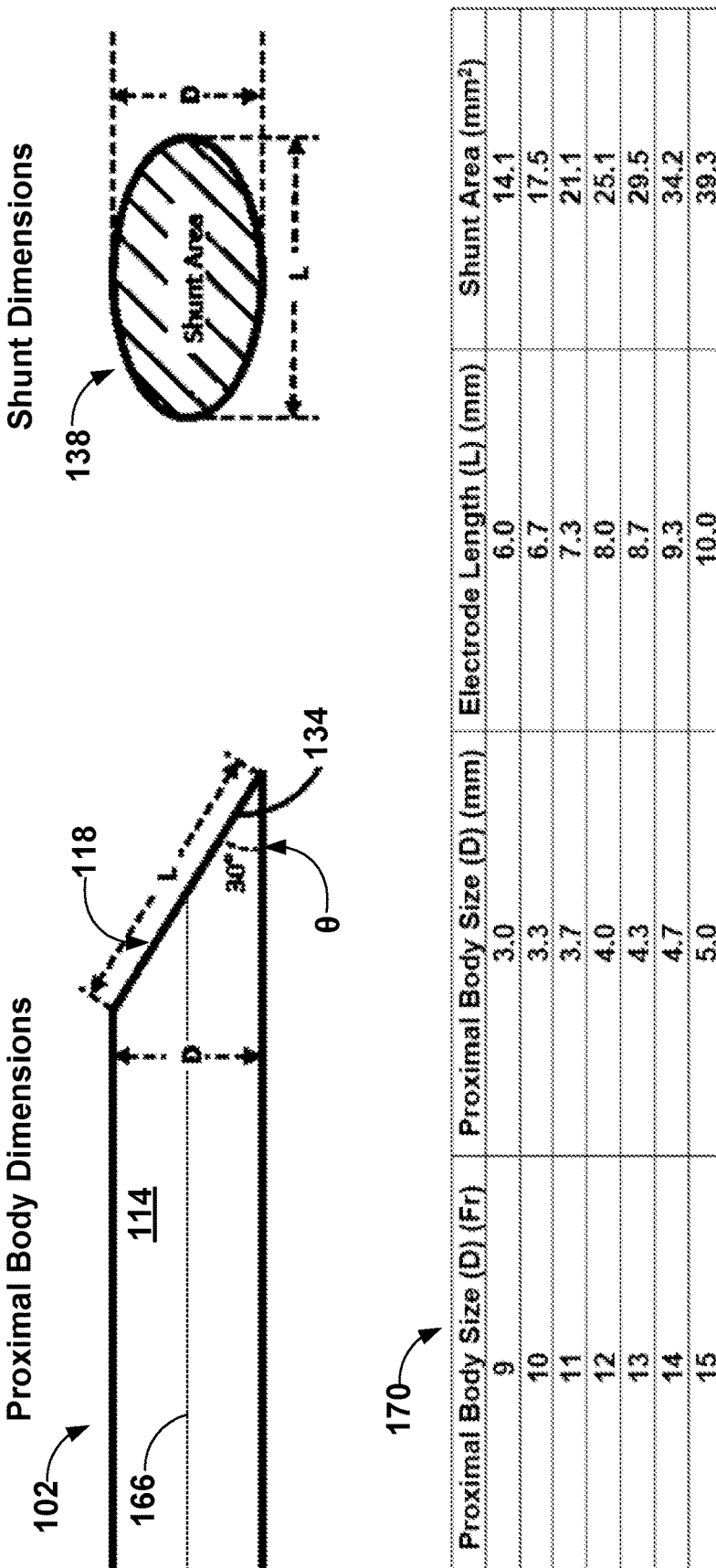
FIG. 3 is a schematic diagram illustrating some example dimensions of the ablation device of FIG. 1.

FIG. 3 is a schematic diagram illustrating some example dimensions of ablation device 102 of FIG. 1. In particular, FIG. 3 includes a chart 170 listing some example dimensions for a cross-sectional diameter D of proximal body 116, listed in units of French (Fr) and millimeters (mm). As indicated in FIG. 3, the cross-sectional diameter D of proximal body 116 corresponds to the width of the minor-axis of the resulting oval-shaped or elliptical-shaped shunt 138. Example values for D range from about 9 Fr (3.0 mm) to about 21 Fr (7.0 mm), for instance, from about 13 Fr (4.3 mm) to about 21 Fr (7.0 mm). As referenced above, depending on the selected angle θ of distal-facing surface 118 relative to longitudinal axis 166 of elongated structure 112, length L of the proximal active heating element (e.g., RF electrode) 134, and equivalently, length L of the major axis of the resulting oval-shaped shunt 138, and accordingly, the size of shunt 138, can be adjusted. Example values for length L range from about 6.0 mm to about 10.0 mm. As used here, "about" may be within about 10%, such as within 5% or less, such as about 1%, of the stated value.

Figure 4:
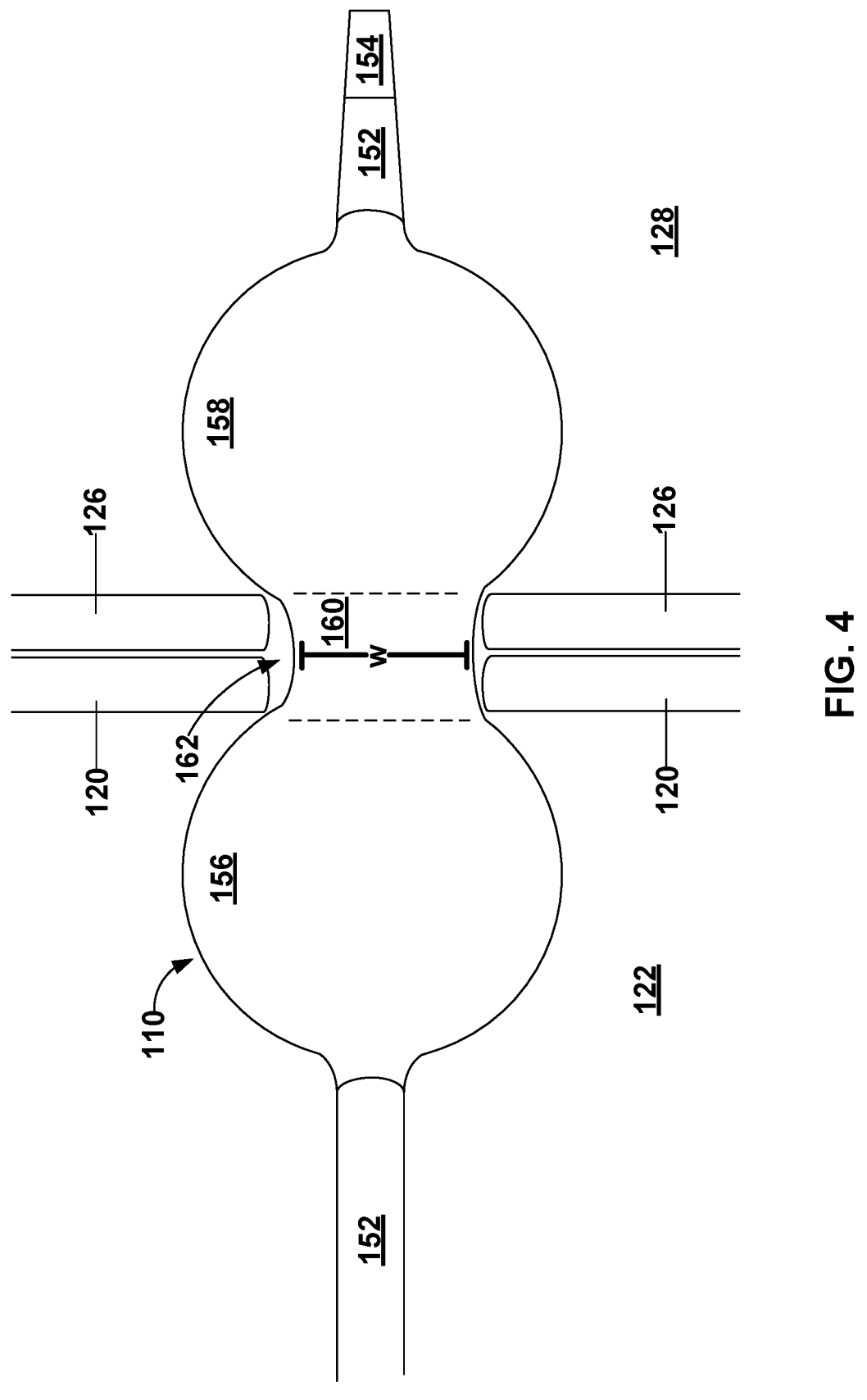
FIG. 4 is a schematic diagram illustrating some example dimensions of an example dilation element of the medical system of FIG. 1.

FIG. 4 is a schematic diagram illustrating an example of puncturing tool 108 and dilation element 110 of medical system 100 of FIG. 1. In some examples, elongated structure 152 of puncturing tool 108 includes or is a guidewire, such as a 0.014-inch (0.3556 mm) to a 0.030-inch (0.762 mm) diameter guidewire. Guidewire 152 can include an electrifiable distal tip 154, such as a radiofrequency (RF) activated plasma tip, configured to heat to form the initial punctures through coronary sinus wall 120 and left atrium wall 126 (FIG. 2). In other examples, electrifiable distal tip 154 is integrated with a distal-most end of dilation element 110, e.g., without a length of guidewire 152 in between.

In some examples, dilation element 110 includes an inflatable balloon configured to inflate with a fluid (e.g., liquid or gas) to expand radially outward within the punctures to dilate the puncture. In the particular example of FIG. 4, the inflatable balloon of dilation element 110 defines a peanut shape or hourglass shape, having a proximal inflatable region 156, a distal inflatable region 158, and a narrower intermediate (e.g., central) region 160 of diameter d therebetween. During use, a clinician can position dilation element 110 such that proximal inflatable region 156 expands while positioned inside of coronary sinus 122, distal inflatable region 158 expands while positioned within left atrium 128, and narrower region 160 expands while positioned within initial punctures 162 between tissues 120, 126. In such configurations, proximal and distal inflatable regions 156, 158 prevent dilation element 110 from slipping or otherwise longitudinally moving (e.g., proximally or distally along longitudinal axis 166 shown in FIG. 1) while inflating to dilate punctures 162. In some examples, central region 160 of dilation element 110 is configured inflate to a diameter d of about 3 mm to about 5 mm, thereby dilating punctures 162 to similar diameters of about 3 mm to about 5 mm.

Figure 5:
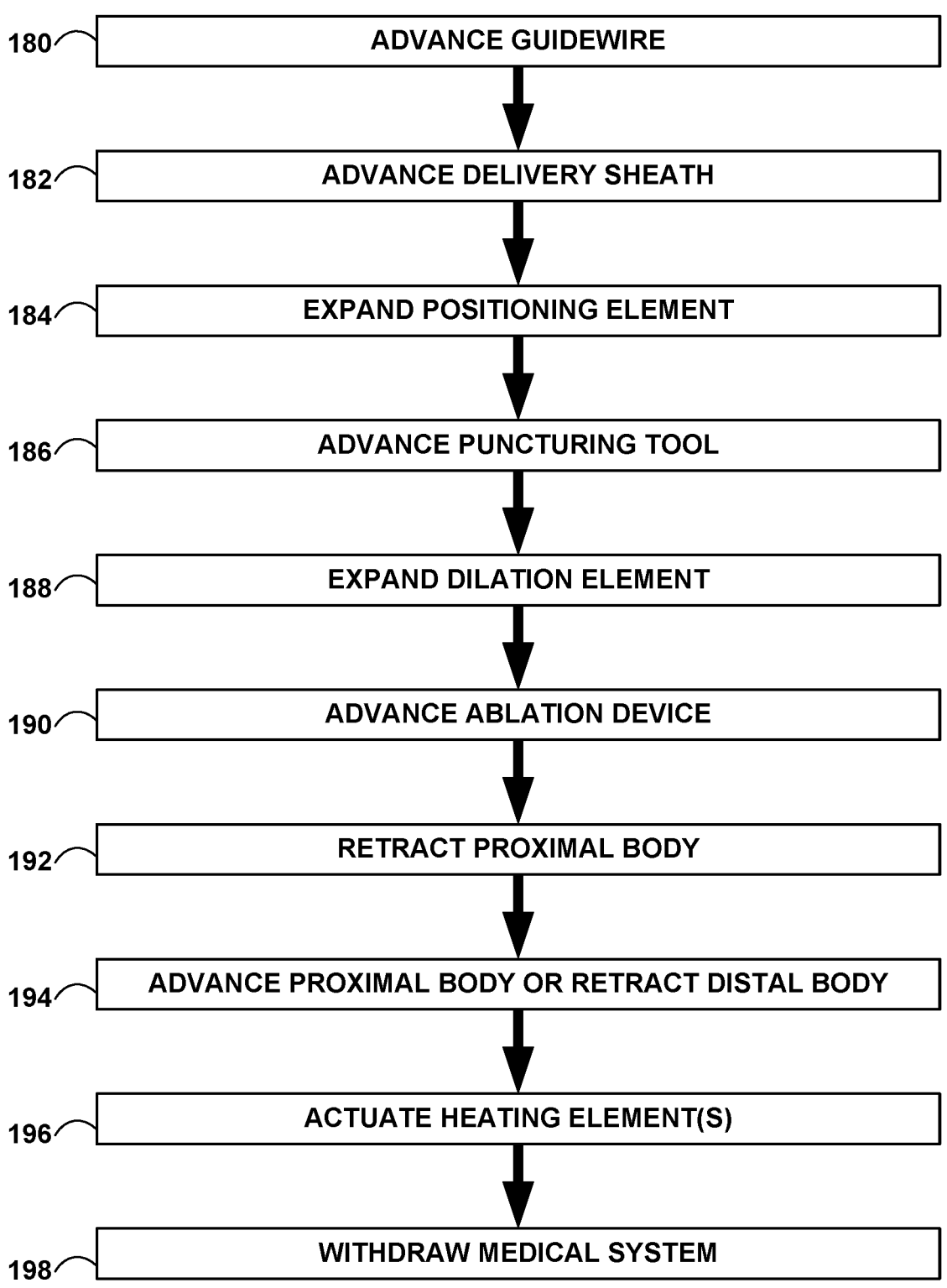
FIG. 5 is a flow diagram illustrating an example technique for forming a shunt between the left atrium of a heart of a patient and the coronary sinus of the patient.
Figure 6A:
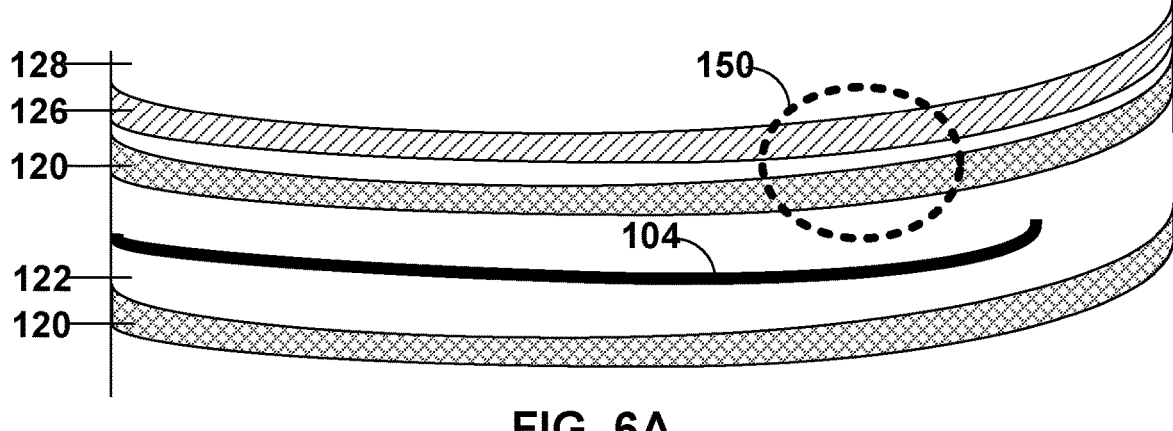
Figure 6B:
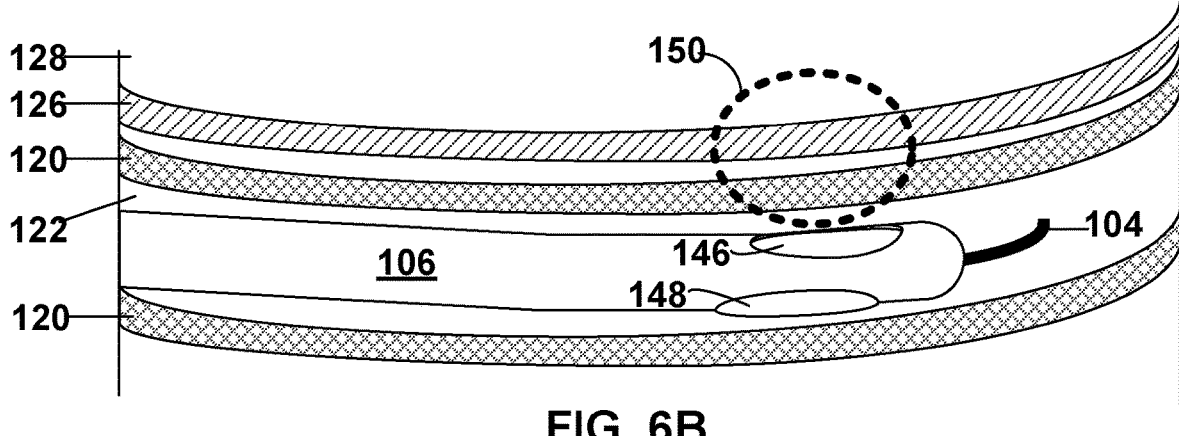
Figure 6C:
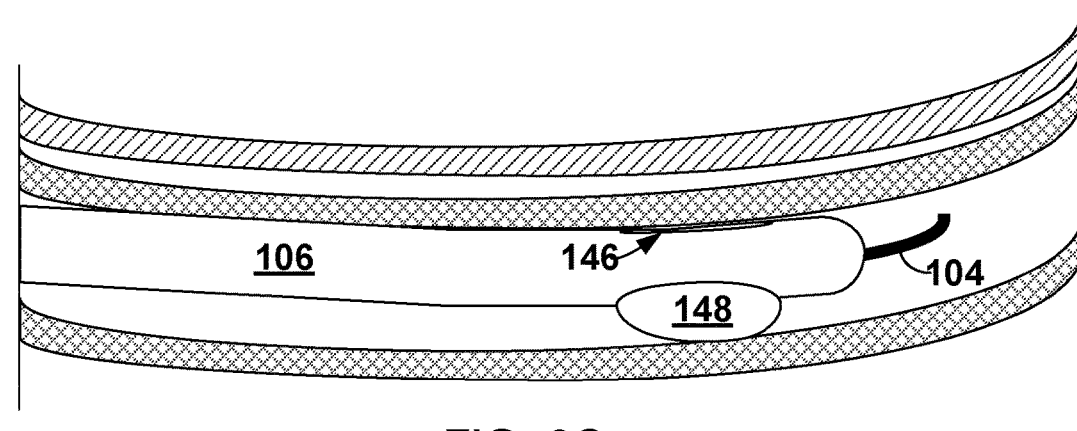

FIG. 5 depicts a flow diagram illustrating an example technique for forming a shunt 138 (FIG. 2) between left atrium 128 of heart 130 of a patient and the patient's coronary sinus 122. The technique of FIG. 5 is described with reference to the conceptual diagrams of FIGS. 6A-6L. For instance, as shown in FIG. 6A, the technique of FIG. 5 includes advancing, by a clinician, guidewire 104 from an entry site in vasculature of a patient to target treatment site 150 (180). For example, a clinician can advance guidewire 104 from the patient's right jugular vein, through the patient's vasculature, and toward target treatment site 150 on an interior surface of coronary sinus wall 120 of coronary sinus 122 (180). As shown in FIG. 6B, the clinician may then advance delivery sheath 106 overtop of guidewire 104 toward target treatment site 150 (182). As shown in FIG. 6C, the clinician may then actuate positioning element 148 of delivery sheath 106 to position side opening 146 of delivery sheath 106 proximate, or even in contact with, target treatment site 150 (184).

Figure 6D:
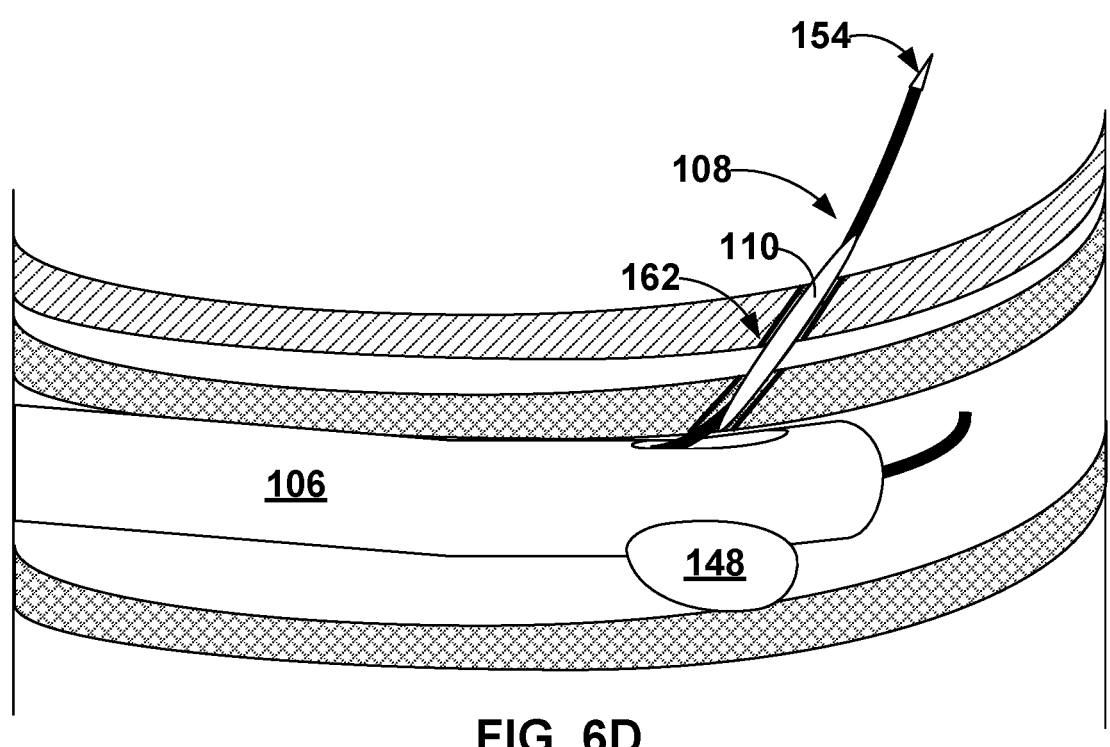
Figure 6E:
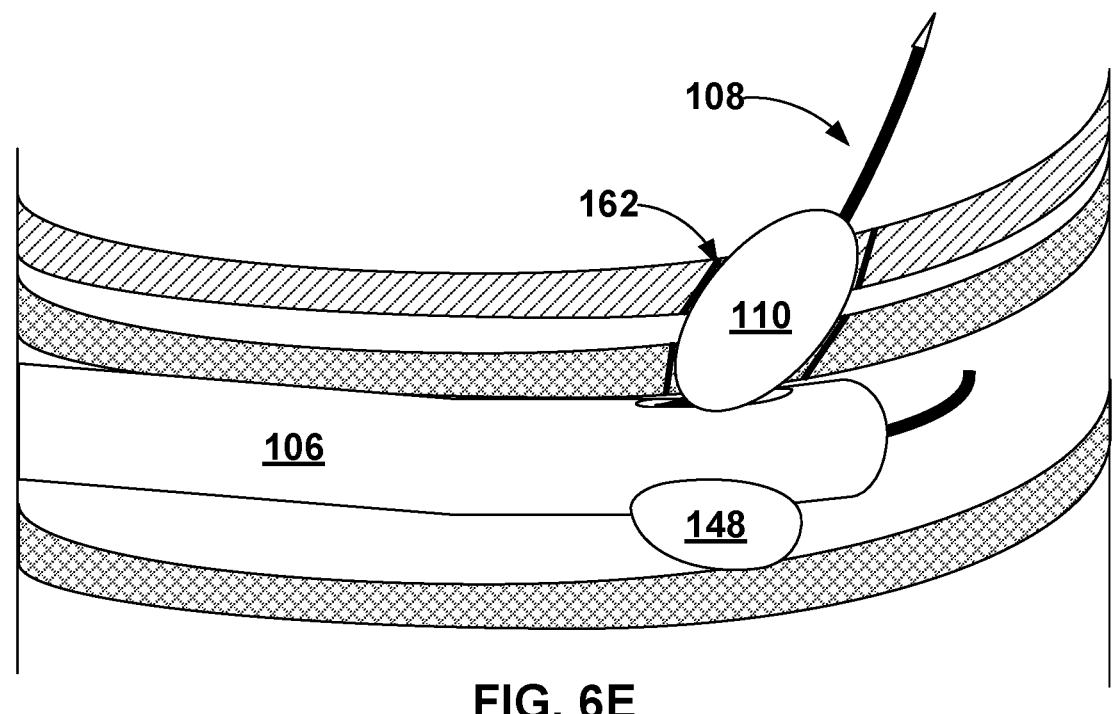

As shown in FIG. 6D, in some examples, but not all examples, the clinician may advance a puncturing tool 108, which may include an electrifiable distal tip 154 or another tip configured to define a pathway through tissue of a patient, through side opening 146 of delivery sheath 106, in order to form an initial puncture 162 through coronary sinus wall 120 and left atrium wall 126 (186). As shown in FIG. 6E, the clinician positions dilation element 110, such as an inflatable balloon coupled to puncturing tool 108, within punctures 162, and expands dilation element 110 to dilate punctures 162 (188). Although dilation element 110 is shown as a balloon with a center portion that is the most radially expanded, in other examples, dilation element 110 can have the hourglass or peanut configuration shown in FIG. 4.

Figures 7A, 7B:
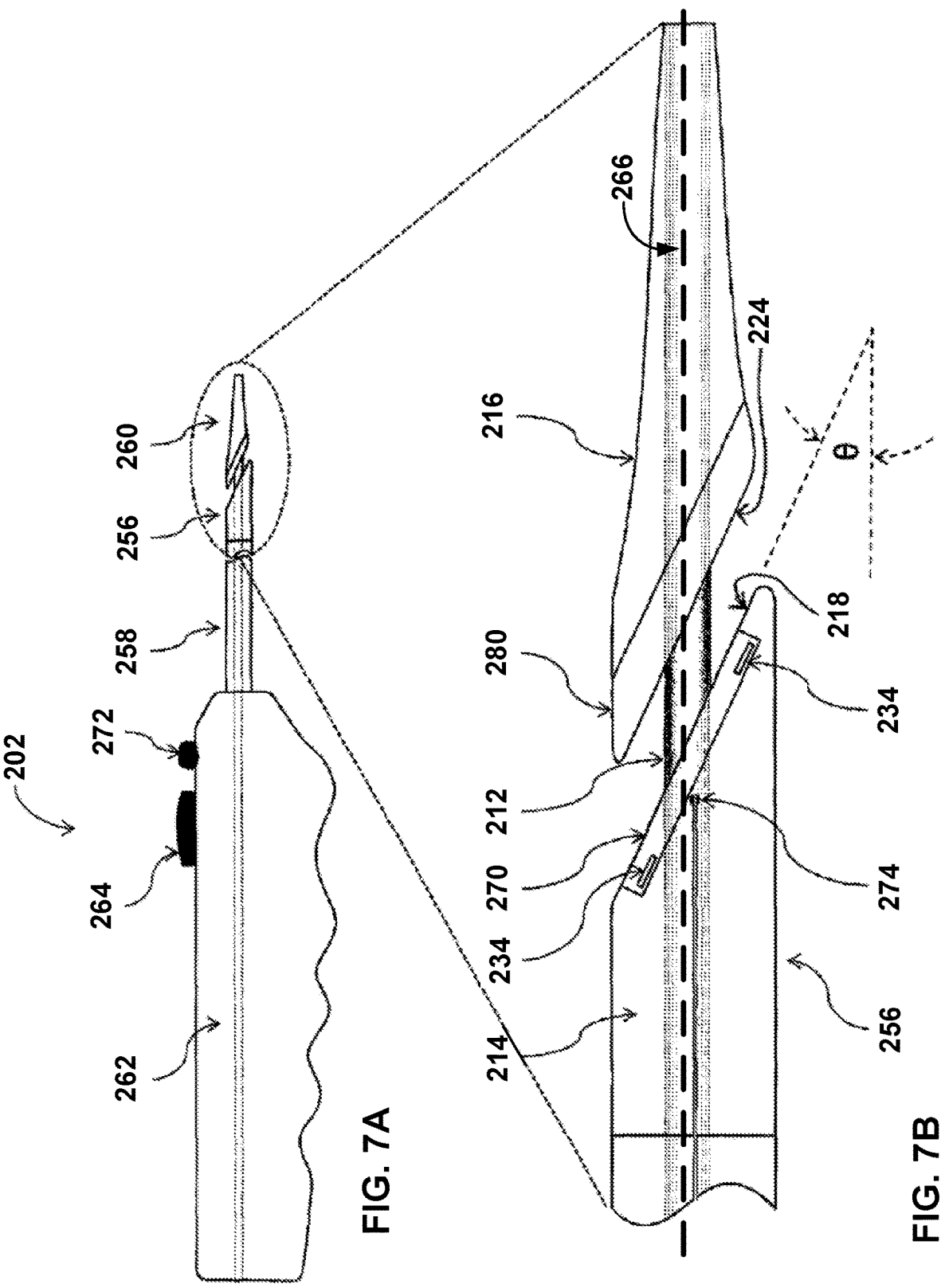
FIG. 7A is an elevational view of another example of the ablation device of the medical system of FIG. 1.
FIG. 7B is an elevational enlarged view of an example distal portion of the ablation device of FIG. 7A.

As shown in FIGS. 6F-6H, the clinician advances an ablation device 102, having a proximal body 114 and a distal body 116, through delivery sheath 106 (e.g., overtop of guidewire 104, puncturing tool 108, or a separate guidewire 132), out from side opening 146, and through dilated punctures 162 (190). In some examples, the clinician may need to use an actuator (not shown in FIGS. 6F-6H) of ablation device 102 (e.g., located on handle 262 of FIG. 7A, described below) to bend, deflect, or otherwise guide distal body 116 away from longitudinal axis 166 of elongated structure 112, and outward through side opening 146. Additionally or alternatively, distal body 116 can include a pre-shaped distal tip, e.g., formed from a shape-memory material, such as Nitinol, that preferentially deflects towards the left atrium 128 during deployment. For instance, distal body 116 may be formed from a soft polymer material with an embedded, pre-shaped, Nitinol flat wire configured to deflect away from longitudinal axis 166 and into left atrium 128. As particularly illustrated in FIG. 6G, the embedded, pre-shaped shape-memory wire 132 may be configured to enable distal body 116 to perform an approximately 90-degree turn from the inner lumen of sheath 106 and outward through sheath side opening 146 toward the target treatment site 150. The relatively flexible distal tip provided by wire 132 or another flexible guide member may facilitate a relatively smooth transition from the inner lumen of sheath 106 (positioned in coronary sinus 122) to left atrium 128, which may require the approximately 90-degree turn in some examples.

Figure 6I:
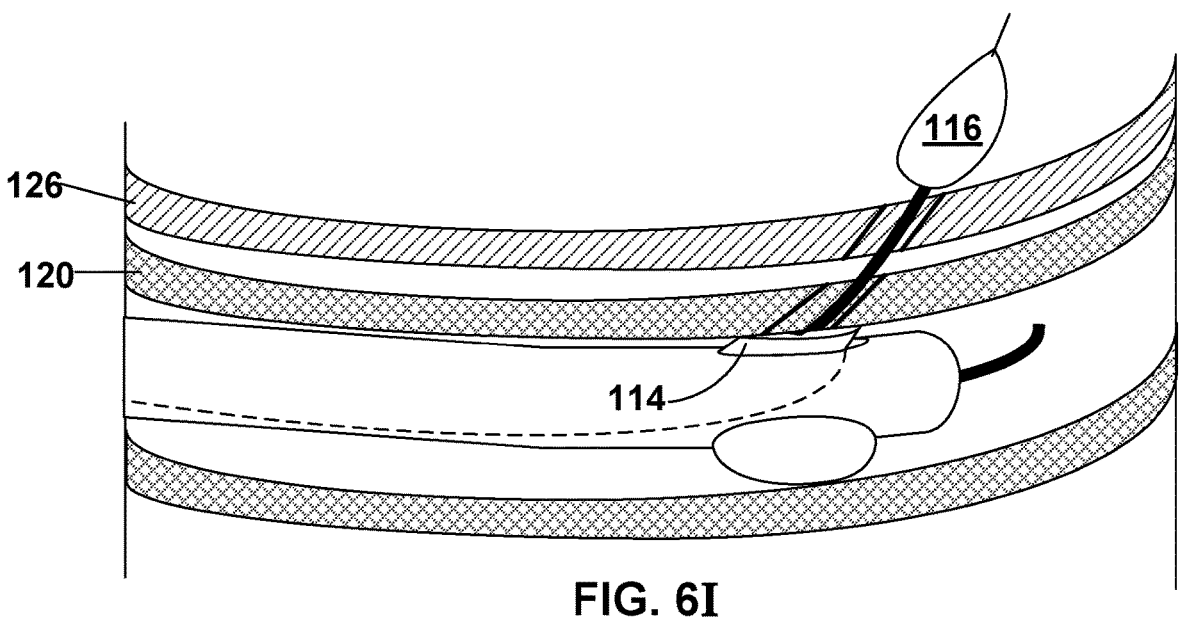
Figure 6J:
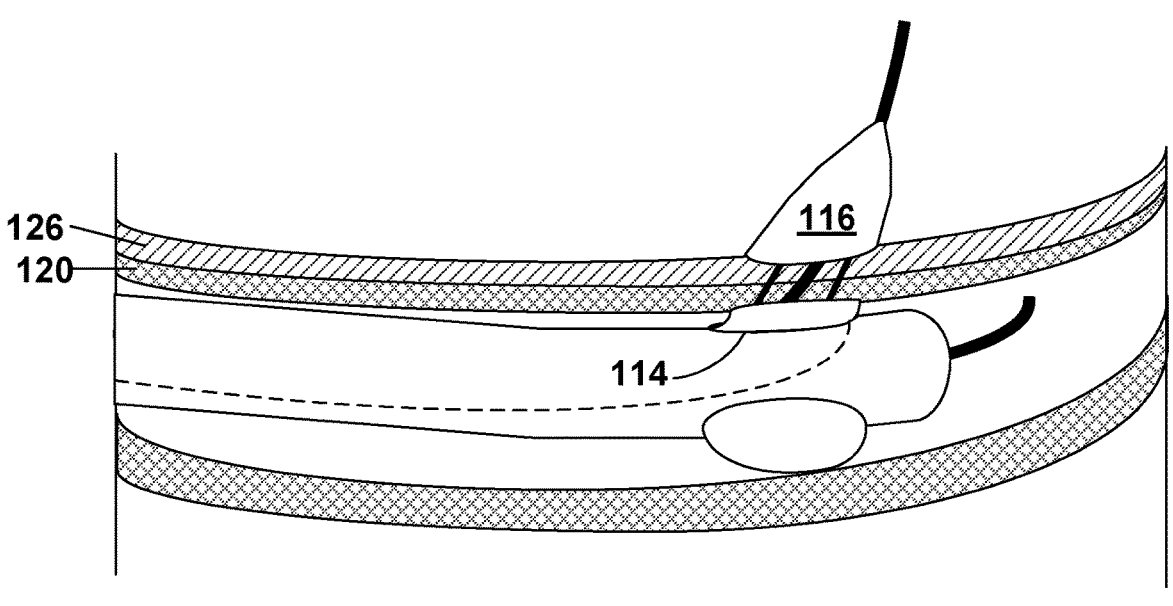

As shown in FIGS. 6I and 6J, the clinician may use a proximal actuator (not shown) located on handle 262 (FIG. 7A, below) to proximally retract proximal body 114 (192) back through punctures 162, and then either distally re-advance proximal body 114 or proximally retract distal body 116, such that coronary sinus wall 120 and left atrium wall 126 are compressed (e.g., sandwiched) between proximal and distal bodies 114, 116 of ablation device 102 (194).

Figure 6K:
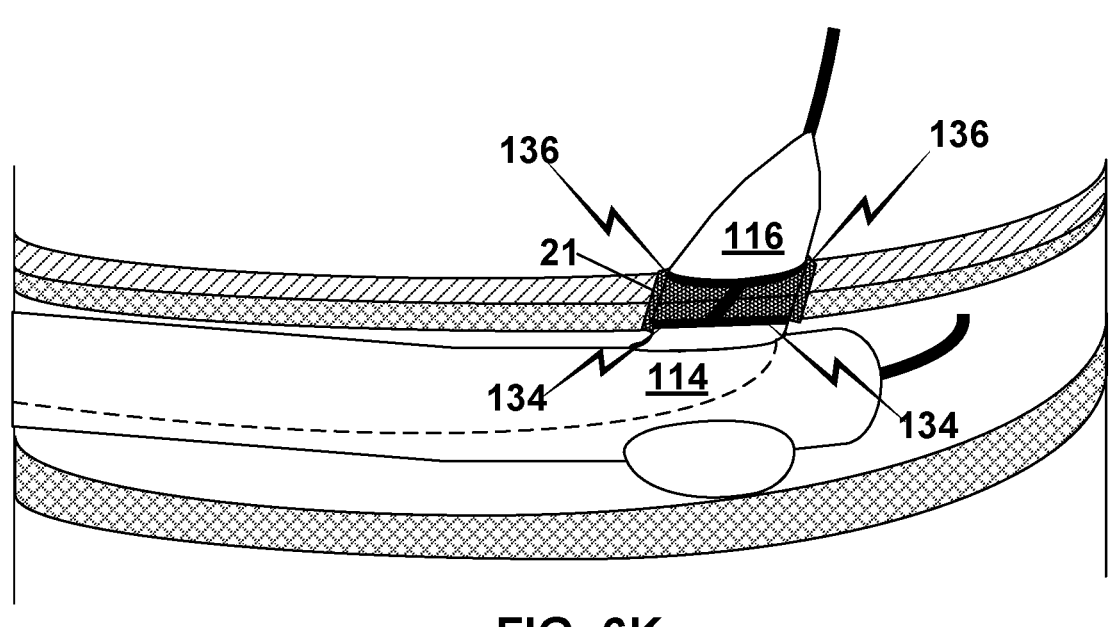
Figure 6L:
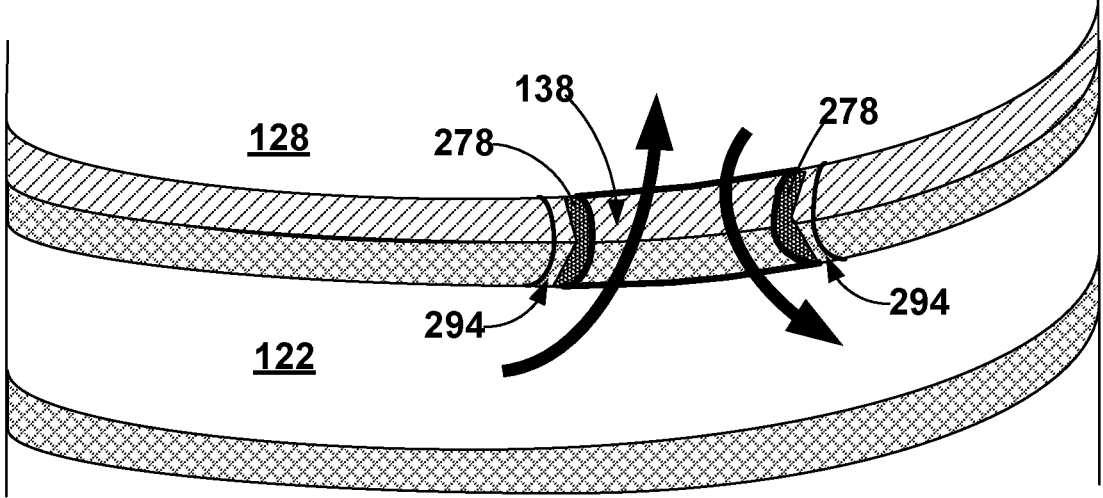

As shown in FIG. 6K, the clinician actuates (e.g., via actuation button 264 on handle 262 of FIG. 7A, below) a pair of opposing proximal and distal heating elements (e.g., electrodes) 134, 136 on proximal and distal bodies, respectively (196). For example, the clinician may cause RF generator 164 to generate and deliver RF energy to proximal heating element 134 and, in some examples, distal heating element 136 as well. As shown in FIG. 6L, the resultant applied heat and pressure from ablation device 104 forms a shunt 138 with welded or coagulated edges 278 defining the perimeter of the shunt opening 138. The clinician then withdraws medical system 100, including ablation device 102, from the patient's vasculature (198).

FIGS. 7A-15 illustrate examples of an ablation device 202, which is itself an example of ablation device 102 of medical system 100 of FIG. 1, except for the differences noted herein. For instance, similar to ablation device 102 of FIG. 1, ablation device 202 includes elongated structure 212 (e.g., elongated structure 112 of FIG. 1), proximal body 214 (e.g., proximal body 114 of FIG. 1), distal body 216 (e.g., distal body 116 of FIG. 1), distal-facing surface 218 (e.g., distal-facing surface 118 of FIG. 1), proximal-facing surface 224 (e.g., proximal-facing surface 124 of FIG. 1), and proximal heating element 234 (e.g., proximal heating element 134 of FIG. 1). In contrast to ablation device 102 of FIG. 1, ablation device 202 includes only a passive (e.g., unpowered) distal heat spreader or surface 280 without an active distal heating element, as detailed further below. In other examples, such as the example ablation device 302 depicted in FIGS. 17A and 17B, the ablation device includes an active distal heating element instead of, or in addition to, passive distal heat spreader or surface 280. In the various examples described below, one or more components of ablation devices 202, 302 may include structures and/or functionality similar to those described in commonly assigned U.S. Pat. No. 9,439,710, granted Sep. 13, 2016, the entire content of which is incorporated herein its entirety.

As shown in FIGS. 7A-8B, ablation device 202 includes a proximal heating assembly 256, a proximal shaft 258, a distal heating assembly 260, and a handpiece or handle 262. As used herein, a "heating assembly" is a component that includes an "active" heating element (e.g., an electrifiable RF electrode, or the like), a "passive" heating element (e.g., a thermally conductive surface configured to redistribute heat received from an active heating element), or an inte-grated combination of such active and passive heating elements. Proximal heating assembly 256 is positioned on distal-facing surface 218 of proximal body 214 and includes proximal heating element 234. Distal heating assembly 260 includes distal body 216 and passive heat spreader 236. Handle 262 includes user interface elements configured to facilitate movement of distal body 216 relative to proximal body 214 (e.g., in a direction proximal body 214 to facilitate the heating of tissue to create shunt 138 (FIG. 2) and in a direction away from proximal body 214). For example, handle 262 can include an actuation button 264 and a release button 272.

Distal-facing surface 218 of proximal body 214 is ori-ented an oblique (e.g., acute) angle θ relative to a longitu-dinal axis 266 of elongated structure 212. In one example, the distal-facing surface 218 is oriented at an angle θ of about 15 degrees to about 90 degrees relative to the longi-tudinal axis 266, such as about 15 degrees to about 50 degrees, for instance, about 23 degrees relative to the longitudinal axis 266. However, the angle θ can be adjusted depending on the particular anatomy of the target treatment site 150 (FIG. 2) and desired dimensions of the resulting shunt 138. These example angles result in an oval-shaped or ellipse-shaped configuration for the shunt 138, and increases the surface areas of the cutting surfaces of device 202 while also efficiently utilizing available heating energy to create an effective cut and peripheral welding zone.

Proximal heating element 234 can be connected to distal-facing surface 218 of proximal body 214 using any suitable technique. For example, proximal heating element 234 can be embedded in, adhered to, or otherwise connected to distal-facing surface 218. Proximal body 214 can be con-structed of a thermally insulating material that is resistive to relatively high temperatures. Example suitable materials for such applications include Vespel® polyimide from DuPont™ of Wilmington, Delaware; Celazole® polybenz-imidazole available from Aetna Plastics of Valley View, Ohio; Teflon™ polytetrafluoroethylene (PTFE) available from The Chemours Company of Wilmington, Delaware; Ultem® polyetherimide available from Curbell Plastics of Orchard Park, New York; and ceramics.

Figures 9A, 9B:
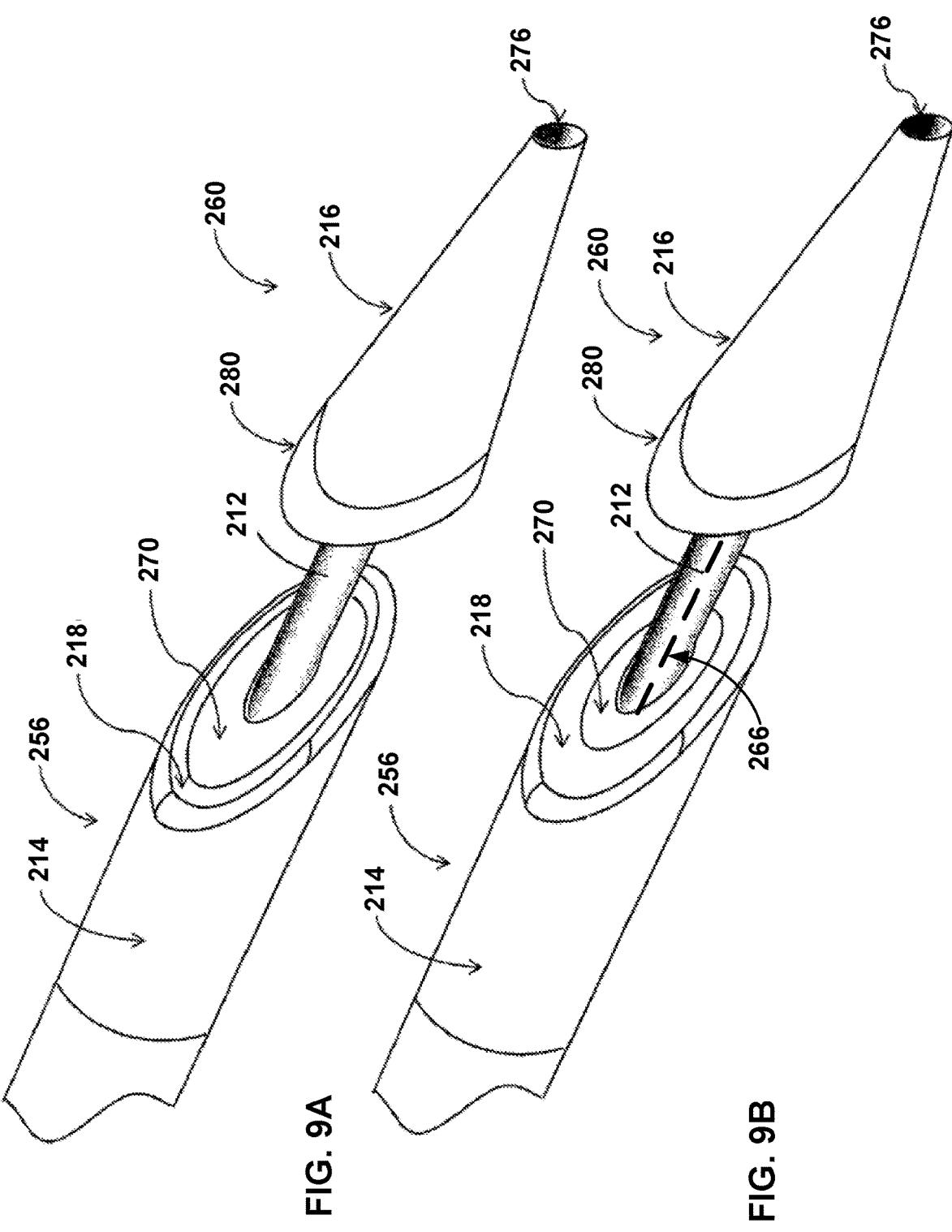
FIG. 9A is an isometric view of another example of the ablation device shown in FIGS. 7A-8B.
FIG. 9B is an isometric view of another example of the ablation device of FIG. 9A.

In some examples, but not all examples, proximal heating assembly 256 includes a proximal "passive" heat-spreader surface 270 configured to compress and heat tissue of coronary sinus wall 120 and left atrium wall 126 (FIG. 2) to create coaptation of the patient tissues. This process can be referred to as "tissue welding" or "tissue fusion." In some examples, proximal heat spreader 270 is constructed of a thermally conductive material with the resistive heating element 234 embedded therein. Some examples of thermally conductive materials suitable for this purpose include, but are not limited to, aluminum, stainless steel, aluminum nitride, or other metal or ceramic materials. The position, size, and shape of proximal heat spreader 270 can be adjusted to control where the heat is applied to tissue (see FIGS. 9A and 9B for additional examples). For example, proximal passive heat spreader 270 may be positioned near the center of the longitudinal axis 266 of the elongated structure 212 (as shown in FIG. 9B), such that a heat gradient is created across the face of angled distal-facing surface 218 of proximal body 214. This helps provide the patient tissue near the center of the cutting region with the most heat, which denatures the tissue, and less heat radially outward from the center, to reduce an amount of tissue necrosis, while still providing strong coaptation or welding of the tissues.

In some examples, proximal body 214 includes a ther-mocouple or temperature sensor 274 configured to monitor the temperature near the active proximal heating element 234, thereby enabling closed-loop temperature control to improve tissue welding and cutting. For example, control circuitry 172 of RF generator 164 of FIG. 1 is configured to deliver RF energy to active heating elements described herein, can further be configured to receive a signal from the sensor 274, the signal being indicative of the temperature near the proximal heating element 234 and adjust an amount of RF energy delivered to the proximal heating element 234 based on the sensed temperature.

Figures 8A, 8B:
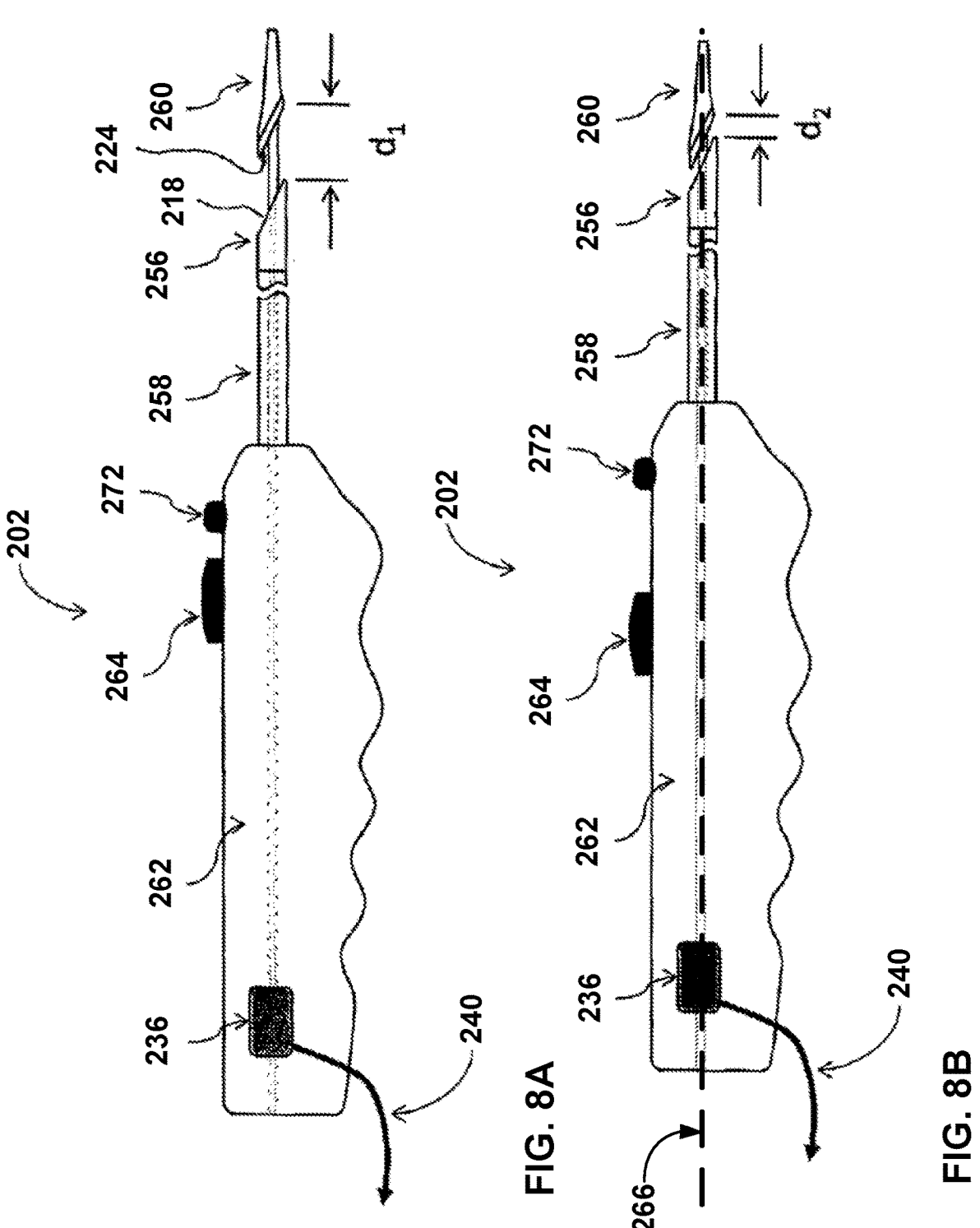
FIG. 8A is an elevational view of an example of the ablation device shown in FIGS. 7A and 7B with the distal end in a first working configuration.
FIG. 8B is an elevational view of the ablation device of FIG. 8A, with the distal end in a second working configuration.

The example ablation device 202 illustrated in FIGS. 8A and 8B may be configured to provide distal-body feedback. For instance, a longitudinal movement of distal heating assembly 260 (e.g., relative to target treatment site 150 or relative to proximal heating assembly 256) may be converted to a signal by a position sensor 236 (e.g., within handle 262, or, alternatively, outside of handle 262. Sensor 236 may include, as non-limiting examples, a linear variable differential transformer (LVDT), a linear potentiometer, a digital caliper, a pressure sensor, a Hall sensor, a magnetic sensor, a magnetoresistive sensor, an ultrasonic sensor, a laser, a piezoelectric sensor, a transceiver, and/or any other type of position sensor configured to detect the displacement of distal body 216 relative to proximal body 214.

Figure 16:
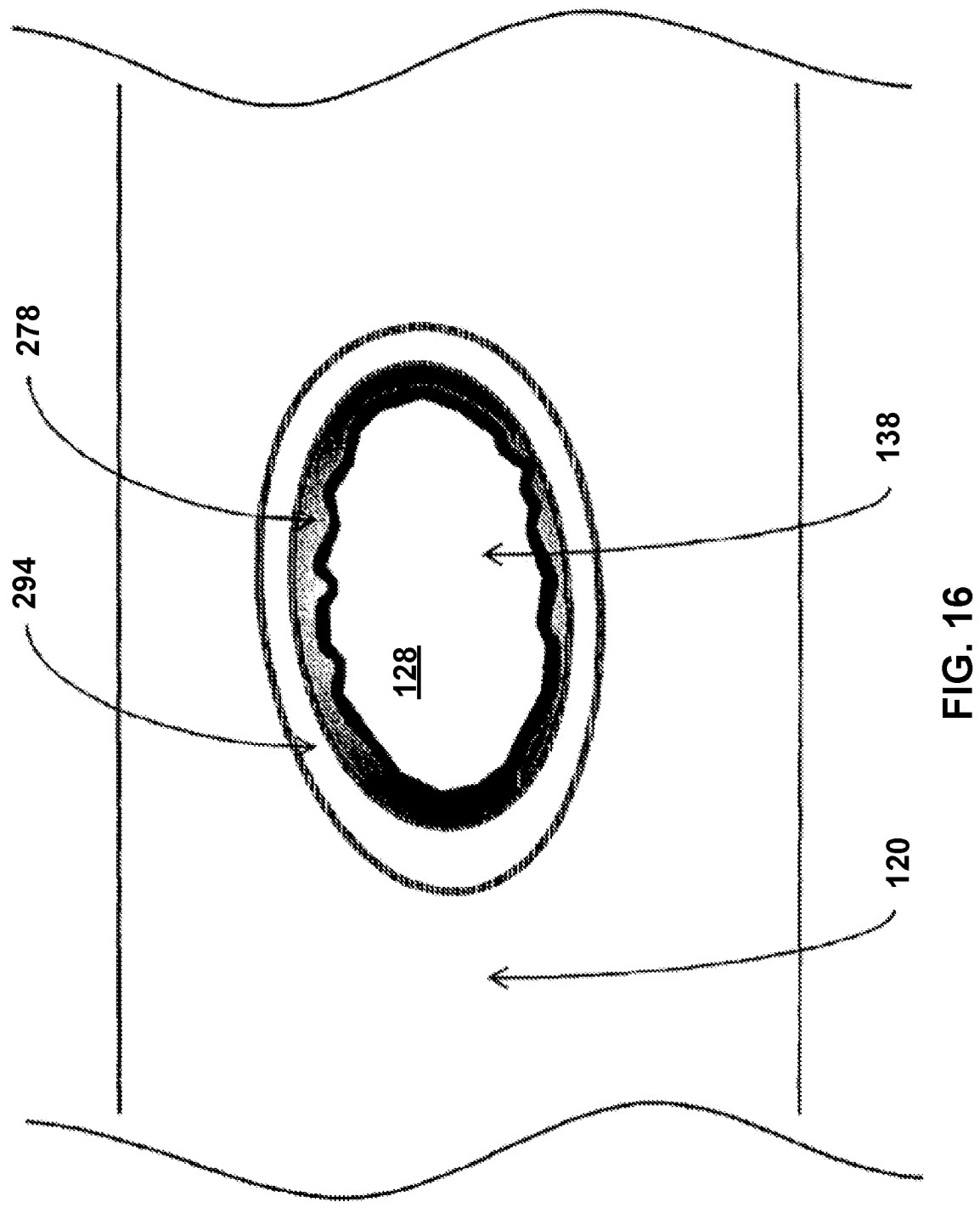
FIG. 16 is a conceptual diagram of a shunt created using example systems and techniques of this disclosure.

Control circuitry 172 of RF generator 164 can then generate and output for display an indication of this longitudinal movement, and/or utilize the signal for a control algorithm to enable one or more automatic functionalities of RF generator 164. For instance, control circuitry 172 can use a signal that relays the absolute position of distal heating assembly 260 from position sensor 236 to a display device (not shown) and through an output signal cable 240 to verify the position of distal body 216 throughout the procedure and help determine (e.g., measure) the thickness of tissues 120, 126 sandwiched between proximal and distal bodies 214, 216 of ablation device 202 before, during, and after the formation of shunt 138 (FIG. 16). The tissue thickness is related to the distance measurement by the equation $T=d*\sin(\theta)$. Accordingly, the tissue thickness before the procedure is correlated to the length of shunt 138 post-procedure.

The relative position of distal heating assembly 260 during the formation of shunt 138 can also be related to the rate of tissue desiccation, cutting, and welding. For instance, the relevant signal may be used as an input to control heat application. For example, in FIG. 8A, proximal heating assembly 256 and distal heating assembly 260 are spaced by a distance $d_1$ prior to the procedure. Based upon the type and thickness of tissues 120, 126 through which shunt 138 is being created, and other factors related to functionality and durability of the shunt, the position of distal body 216 position after the procedure can provide confirmation that the tissues were properly desiccated and both tissue walls 120, 126 have been cut. After the procedure, distal body 216 of ablation device 202 is moved forward to a spaced position $d_2$ (FIG. 8B) for device extraction and the position of distal body 216 can be verified using sensor(s) 236.

In examples such as those shown in FIGS. 9A and 9B, elongated structure 212 of ablation device 202 includes a non-stick surface configured to help prevent coagulated blood and tissue from bonding to the surface and obstructing the annular section of distal-facing surface 218 between the outer diameter of elongated structure 212 and the inner diameter of proximal active heating element 234. If blood or tissue bonds to or obstructs this annular section of distal-facing surface 218, then it may interfere with effective compressive-force transmission to distal heating assembly 260 and may inhibit the tissue-fusion and/or tissue-cutting functions. In some examples, the outer surface of elongated structure 212 and inner surface of proximal heating element 234 may have a surface finish of less than about 16 Ra; may define an annular section of distal-facing surface 218 of about 0.0005 inches (0.0127 mm) to about 0.0002 inches (0.00508 mm); and may be coated with a high-temperature, non-stick material, as described above.

Figure 11:
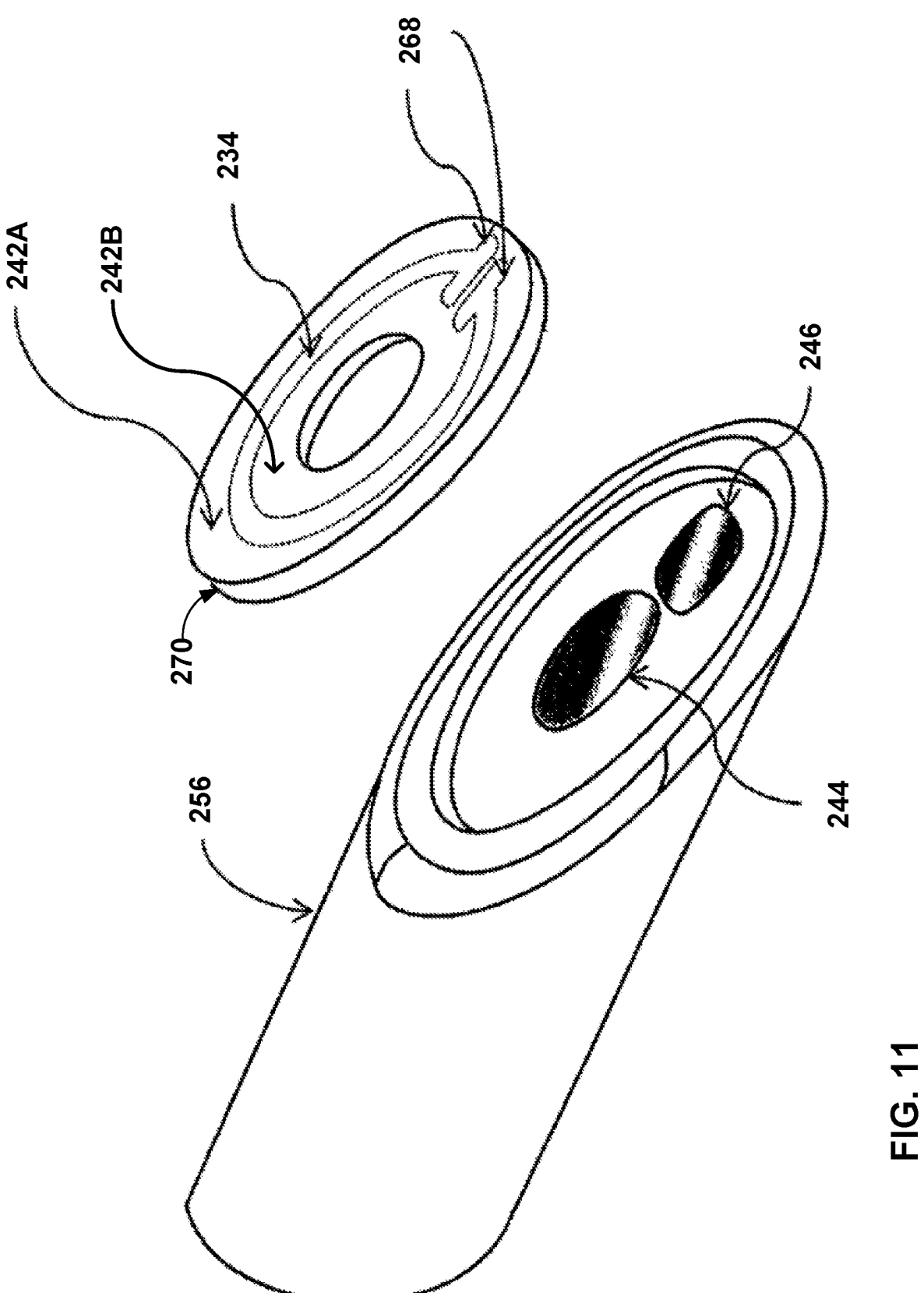
FIG. 11 is an exploded isometric view of another example of the proximal body and heating assembly of FIG. 10A.
Figure 12:
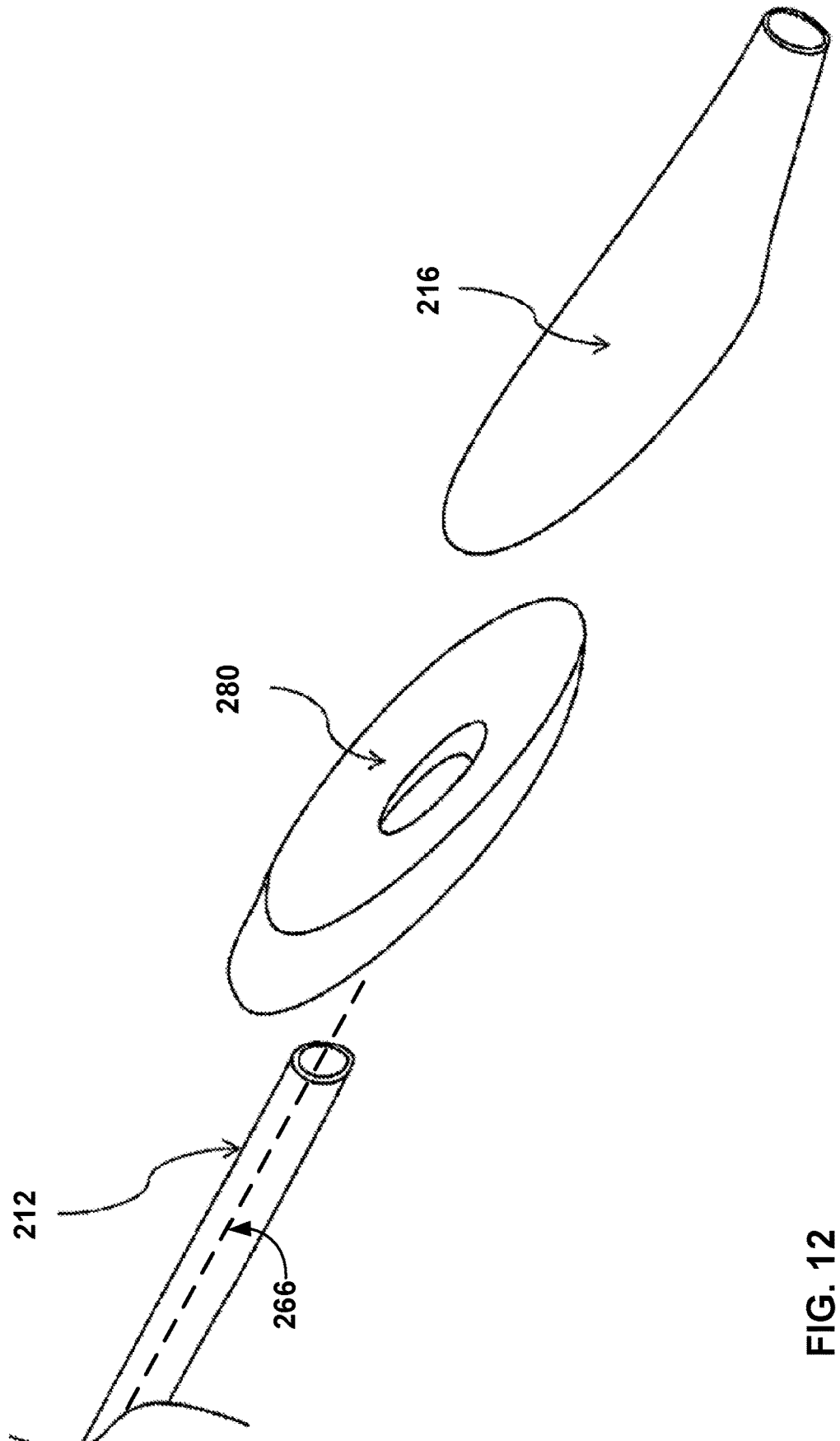
FIG. 12 is an exploded isometric view of an example distal body of the ablation device of FIGS. 7A-8B.

FIG. 11 illustrates an example proximal heating assembly 256, which includes proximal active heating element 234 (e.g., formed from tungsten) sandwiched between two ceramic layers 242A, 242B, collectively forming proximal heat spreader 270.

As further illustrated in FIGS. 12 and 13A-13C, in some examples, distal body 216 includes an outer surface having a generally conical shape, e.g., that tapers distally along longitudinal axis 266. In some examples, such as the examples shown in FIGS. 14A-14F, distal body 216 can have a variable-tapered, sloped outer surface defining a cross-sectional profile (the cross-section taken parallel to longitudinal axis 266) that distally tapers down to the approximate diameter of a guidewire to provide an atraumatic structure for passing through coronary sinus wall 120 and left atrium wall 126 (FIG. 2). In some such examples, a guidewire lumen 276 extends through the center of the distal body 216, as shown in FIGS. 9A and 9B. For instance, as described above, the distal tip of distal body 216 may include a pre-shaped shape-memory flat wire or another elongated guide member configured to cause the relatively soft material of distal body 216 to bend to perform the approximately 90-degree turn from the inner lumen of sheath 106 and out through side opening 146.

Figure 15:
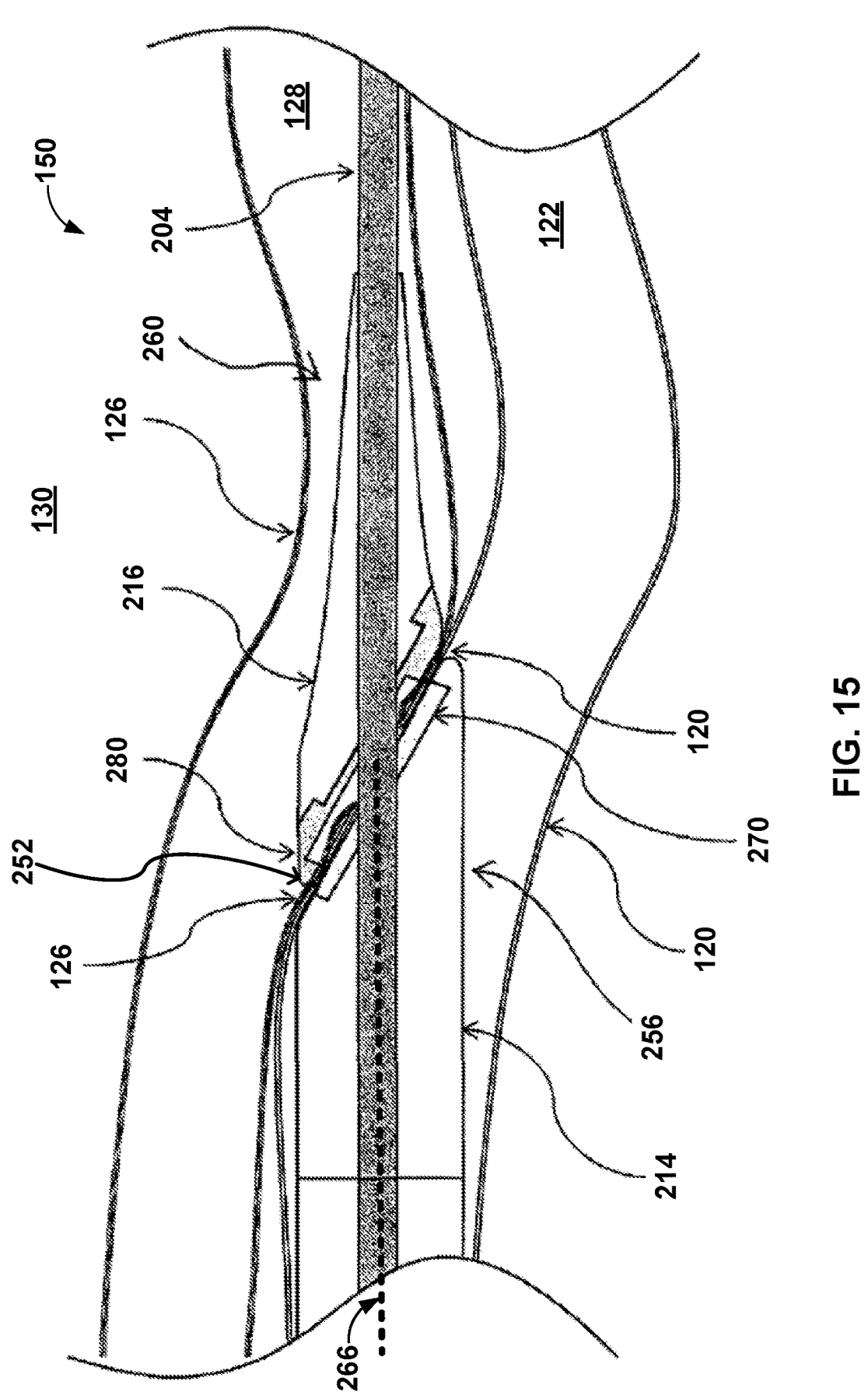
FIG. 15 is a cross-sectional view through the target treatment site of FIG. 2 showing an example application and technique of using the ablation device of FIGS. 7A-8B, wherein the cross-section is taken with an anatomical transverse plane through the patient's heart viewed from a caudal perspective toward the patient's feet.

As shown in FIG. 15, after the clinician has used dilation element 110 to stretch or loosen the initial punctures to be significantly wider than the nominal cross-sectional area of puncturing element 108, ablation device 202 is tracked over a guidewire 204 and the tapered outer surface of the distal body 216 dilates through the coronary sinus wall 120 of the coronary sinus 122 and the left atrium wall 126 of the left atrium 128, and into the left atrium 128 of the patient's heart 130. Once distal heating assembly 260 is completely disposed within left atrium 128, a clinician can retract distal body 216 to bring distal body 216 toward proximal heating assembly 256, thereby capturing tissue from coronary sinus wall 120 and left atrium wall 126 between the proximal and distal bodies 214 and 216, and bringing coronary sinus wall 120 and left atrium wall 126 together. The proximal-facing surface 224 of the distal heating assembly 260 is angled so as to parallel the distal-facing surface 218 of the proximal heating assembly 256.

In some examples, proximal body 214 is configured as shown in FIGS. 9A and 9B, e.g., to receive or otherwise mechanically connect to proximal heating element 234 (FIGS. 10A-10C), which may be at least partially separated from coronary sinus wall 120 by the proximal heat spreader or heating surface 270. That is, in some examples, proximal passive heat spreading surface 270 may cover or physically separate at least part of proximal heating element 234, within distal-facing surface 218, from an external environment. Proximal passive heating surface 270 includes a thermally conductive material which draws and redistributes heat from the proximal active heating element 234. In the example shown in FIG. 9A, proximal passive heating surface 270 encompasses a significant portion of the surface area of distal-facing surface 218. By contrast, in the example shown in FIG. 9B, proximal passive heating surface 270 encompasses a significantly smaller portion of the surface area of distal-facing surface 218, e.g., extends radially outward from longitudinal axis 212 by a smaller amount than in the example of FIG. 9A.

Figures 10A, 10B:
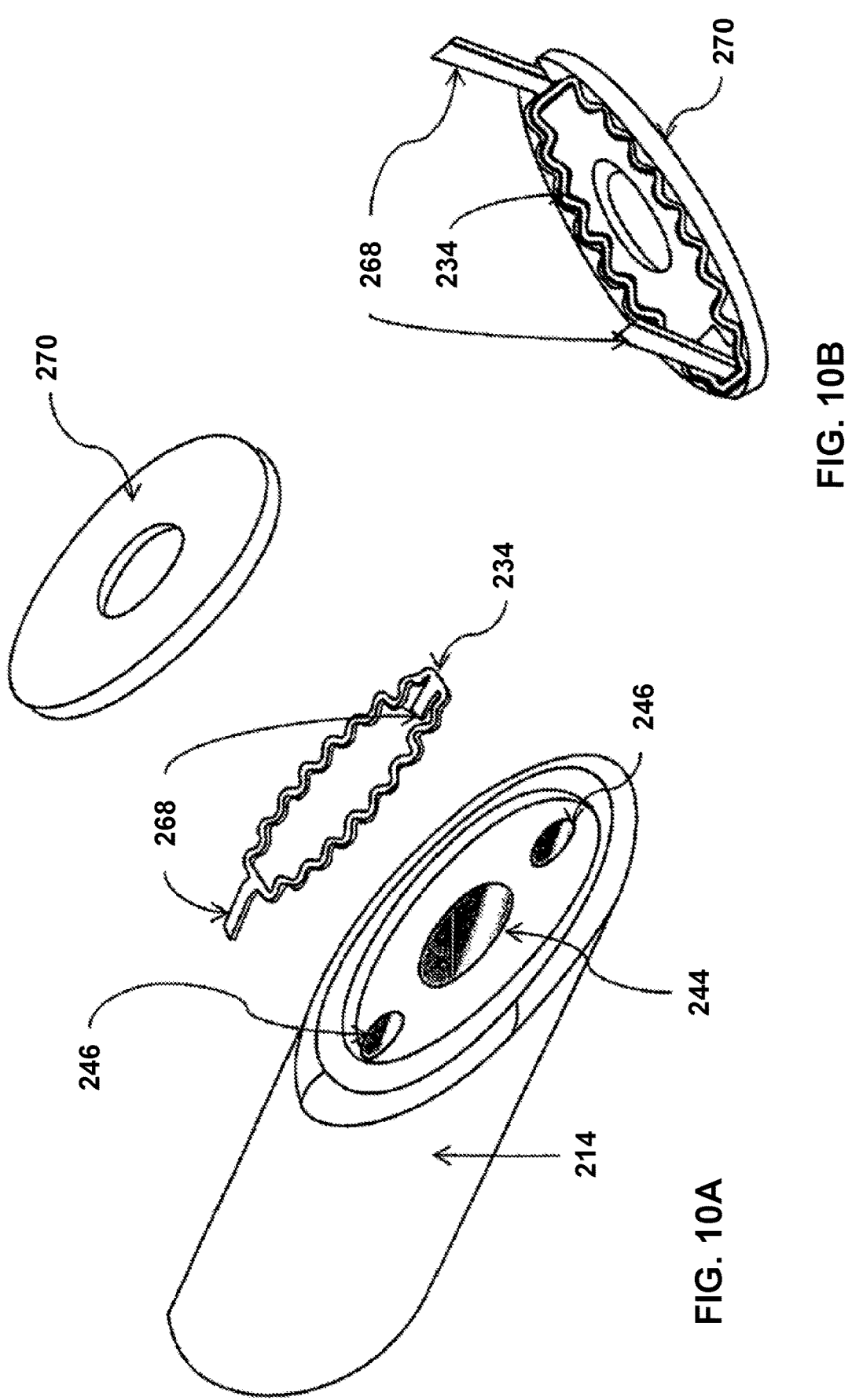
FIG. 10A is an exploded isometric view of an example proximal body of the ablation device of FIGS. 7A-8B, illustrating an example heating element of the ablation device.
FIG. 10B is an isometric view showing the assembled heating element of FIG. 10A.

As shown in FIGS. 10A and 10B, ablation device 202 can include power attachment points 268. Power attachment points 268 are the sub-components of proximal heating element 234 that are electrically coupled (e.g., through conductive wires running proximally through ablation device 202) to RF generator 164. Power attachment points 268 are configured to help ensure that proximal active heating element 234 may be energized with RF energy from RF generator 164. Proximal passive heating surface 270 is configured to transfer heat from heating element 234 into adjoining tissue walls 120, 126 to create a weld band 278 (FIG. 16) and to cut tissue to create shunt 138 (FIG. 2). The size and shape of weld zone 278 and shunt 138 can be altered by adjusting the shape or geometry of proximal passive heating surface 270. This geometry can also be altered such that the temperature is equal in the passive and active heated surfaces 270, 234, respectively.

In some examples, proximal passive heat spreader or surface 270 includes an aluminum plate, although other thermally conductive materials such as aluminum nitride, ceramics, tungsten, steel, or beryllium may additionally or alternatively be used. In some examples, the thickness of proximal passive heating surface 270 (e.g., as measured perpendicular to the plane of distal-facing surface 218) is approximately the thickness of coronary sinus wall 120 in which weld 278 is being created. However, this thickness may be increased or decreased to control the amount of heat that is conducted into the surrounding tissue of coronary sinus wall 120. An example thickness of proximal passive heating surface 270 ranges from about 0.010 inches (about 0.254 millimeters (mm)) to about 0.060 inches (about 1.524 mm) (see FIGS. 9A, 9B, and 10A-10C).

Figures 13A, 13B:
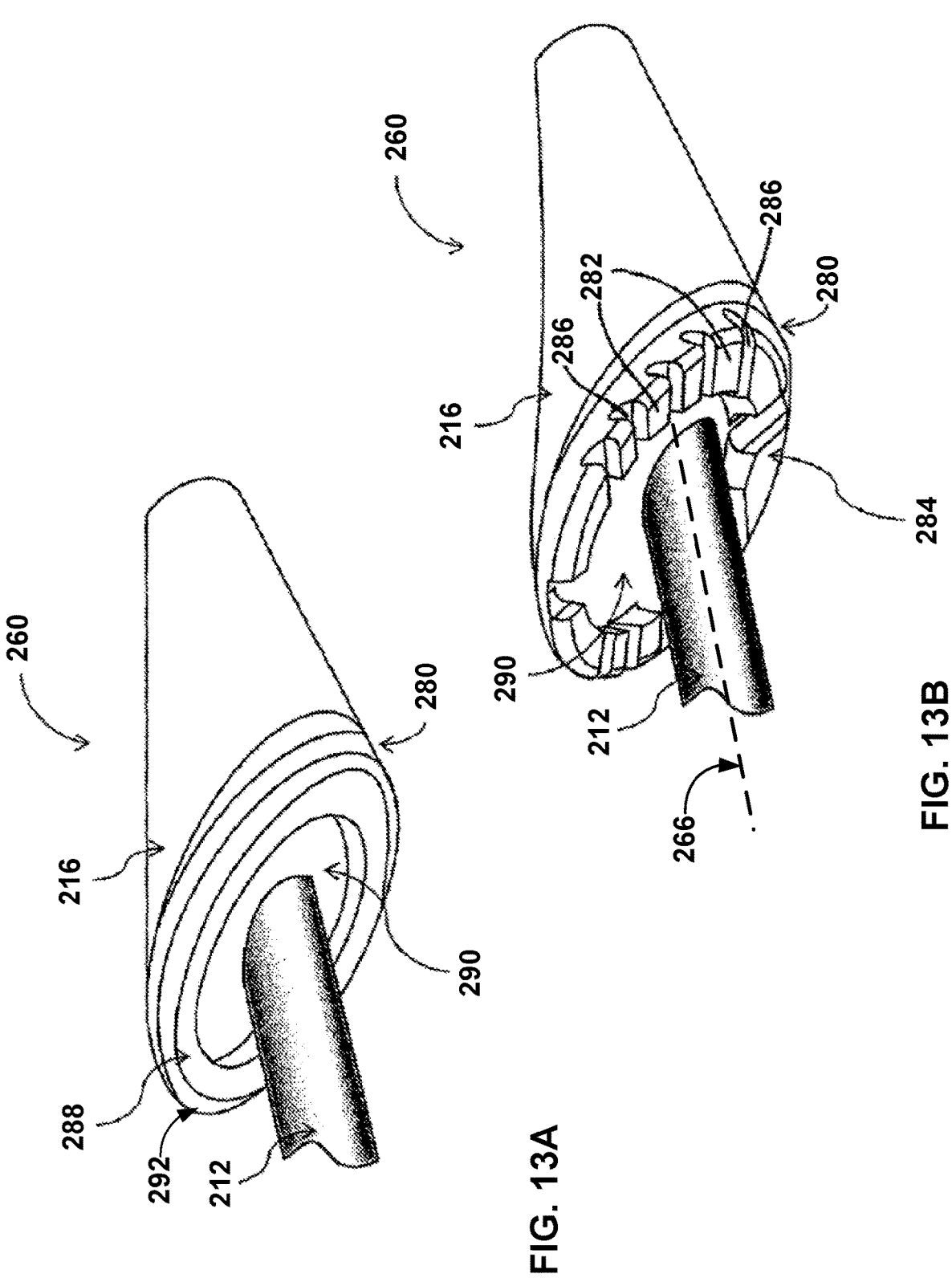
FIG. 13A is an isometric view of an example distal body and an example heating element of the ablation device of FIGS. 7A-8B.
FIG. 13B is an isometric view of the distal tip and heating element of FIG. 13A.

Similar to proximal passive heating surface 270 on distal-facing surface 218 of proximal body 214, in some examples, proximal-facing surface 224 of distal body 216 may include a distal passive heating surface configured to more-precisely distribute heat (e.g., from proximal active heating element 234 and/or from a distal active heating element, if present) into adjoining tissue walls 120, 126 to create shunt 138. For instance, as illustrated in FIG. 13B, in some examples (but not all examples), a distal passive heat spreader 280 on the distal body 216 includes a plurality of raised segments 282 that define forming a segmented distal rib 284. Segmented distal rib 284 is configured to create a focused heat conduction path through the patient tissue, while gaps 286 between segments 282 are configured to provide an insulative barrier that limits tissue desiccation to promote adhesion without cutting. The size and number of raised segments 282 can be adjusted to control the rate of tissue desiccation that may accommodate variable tissue thickness.

Figures 14A, 14B, 14C, 14D, 14E, 14F:
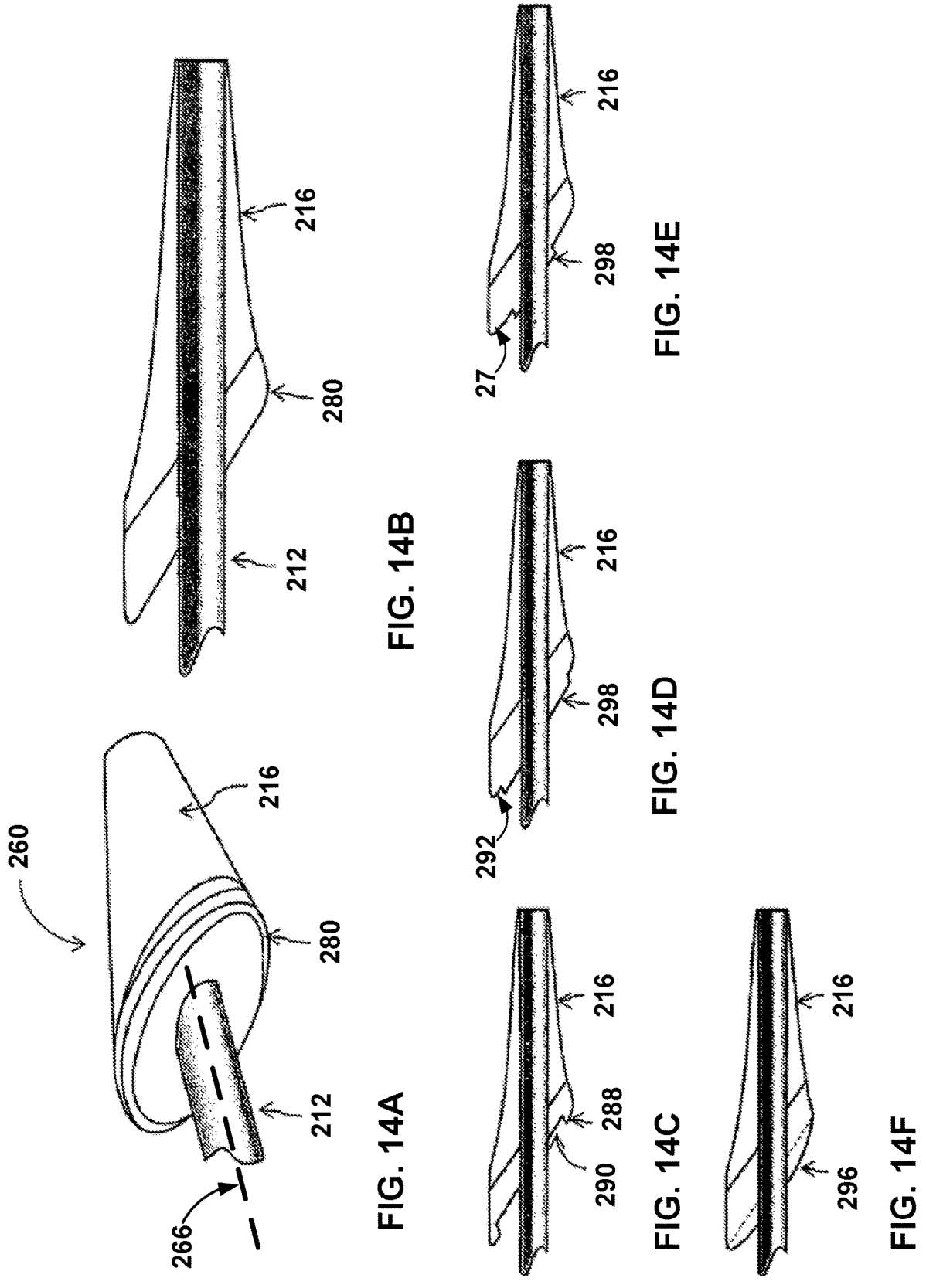
FIG. 14A is an isometric view of another example of the distal body and the heating assembly of the ablation device of FIGS. 7A-8B.
FIGS. 14B-14F are cross-sectional views of different example distal bodies and heating assemblies of the ablation device of FIGS. 7A-8B, the cross-section taken parallel to the longitudinal axis of the device.

In another example, as illustrated in FIGS. 13A and 14C, passive distal heat spreader 280 has a raised outer rib 288 along its circumference. Raised outer rib 288 is configured to create a pocket 290 in the center where tissue is captured and removed during the welding process. An outer circumference of rib 288 has an outer annular-shaped region 292 configured to create an annular transition area 294 (FIG. 16) between weld band 278 immediately outside of the cut zone of the shunt 138 and the native tissues 120, 126 (FIG. 2). Outer annular region 292 allows for minimal compression at the edge of the weld 278. This configuration provides a focused heat conduction path through the tissue between the active and passive heating assemblies to promote tissue cutting, while the step gap provides an offset that limits tissue compression and desiccation in the inner and outer regions to promote tissue adhesion without cutting in the adjacent zone.

In some examples, as illustrated in FIG. 14F, the distal heating assembly 260 has a domed proximal-facing surface 296 (e.g., proximal-facing surfaces 124, 224). The domed shape of the proximal-facing surface 296 creates a higher-compression zone in the center to promote tissue cutting, while tapering off at the perimeter to promote tissue desiccation and adhesion without cutting.

Figure 13C:
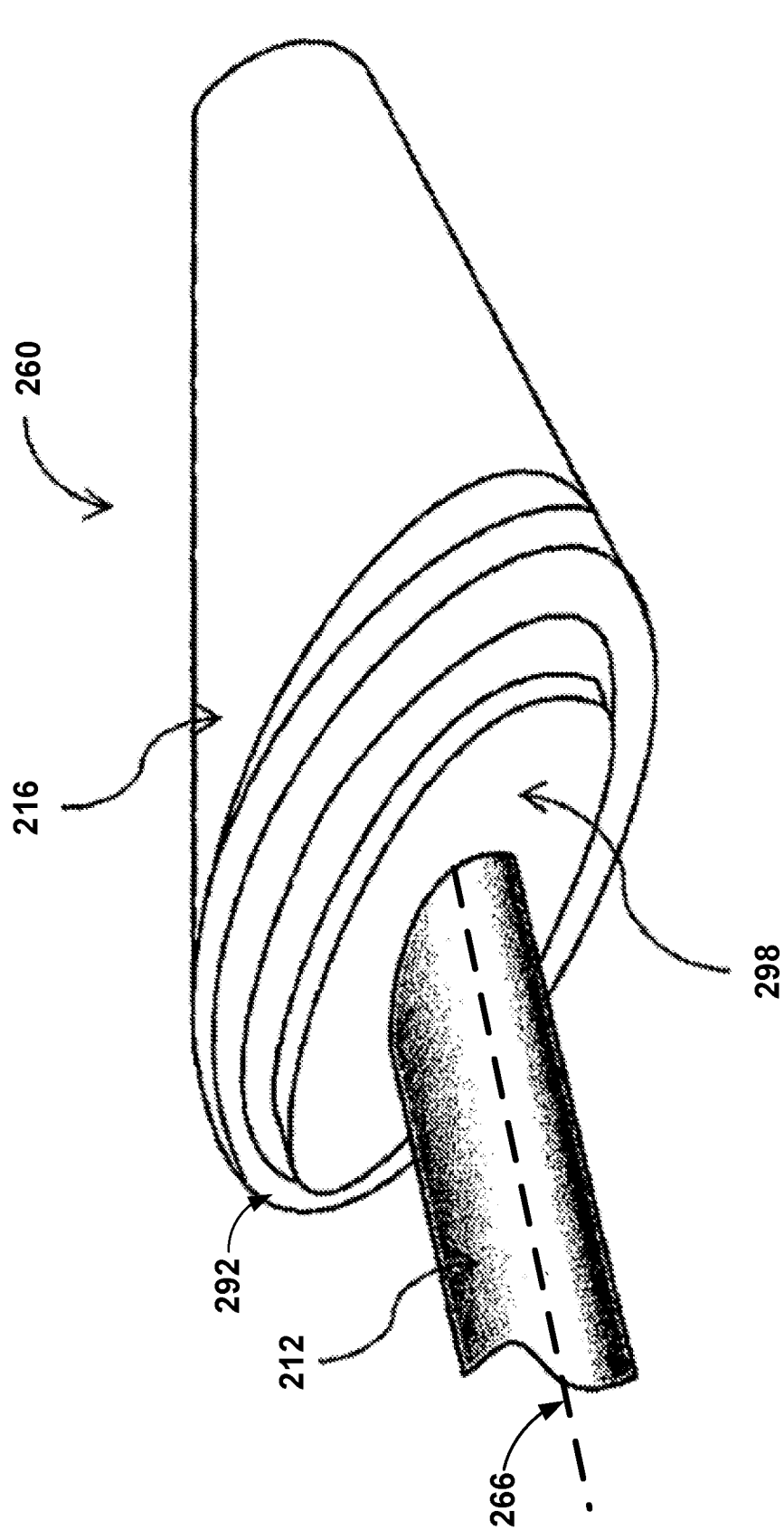
FIG. 13C is an isometric view of another example of the distal body and heating assembly of the ablation device of FIGS. 13A and 13B.

In another example, as illustrated in FIGS. 13C and 14D, a raised proximal-facing surface 298 (e.g., proximal-facing surfaces 124, 224) is configured to increase the compression force on the tissue 126 (FIG. 2) in the center, while creating a wider weld band 278 (FIG. 16) around the perimeter. The wider weld band 278 can help create a stronger weld between coronary sinus wall 120 and left atrium wall 126. The width of raised center section 298 (e.g., as measured in an axial direction along longitudinal axis 266) may be adjusted to be narrower or wider in order to achieve the desired weld strength or geometry of shunt 138. As illustrated in FIG. 14E, a slit between coronary sinus 122 and left atrium 128 can be created by making raised proximal-facing surface 298 extremely narrow. As the surface area of the mating section of distal heating assembly 260 is decreased, the amount of heat transferred from proximal active heater 234 will decrease. This can be useful if less heat is needed between the two anatomical structures 120, 126 that are being welded. Another feature of a narrow raised proximal-facing surface 298 is a temperature gradient across distal heating assembly 260 that increases radially from the raised section. A temperature gradient allows the heat to be the highest at the center, which completely denatures and cuts through tissue, creating a shunt 138. As the temperature decreases radially, tissues 120, 126 may exhibit reduced necrosis, yet the proteins therein remain sufficiently denatured, which leads to a strong weld band 278 and promotes long-term healing.

The shape of distal heating assembly 260, in combination with compression force, influences the rate at which distal passive heating element 280 cuts through the tissue. If too much heat or pressure is applied abruptly, distal heating assembly 260 may quickly cut through the tissue without transferring enough heat to surrounding tissues 120, 126 to achieve a satisfactory weld 278. A balance of heat and pressure desiccates and denatures the protein in the tissue 278 surrounding the cut to promote adhesion prior to cutting. In some examples, to help achieve this balance, medical system 100 includes control circuitry (e.g., control circuitry 172 of RF generator 164) configured to monitor the temperature and position of distal body 216 during the welding process and adjust the heat and/or pressure being applied by ablation device 202 to achieve the desired rate of ablation and to ensure that distal heating assembly 260 and proximal heating assembly 256 are directly opposed to ensure complete weld fusion and aperture cutting. Different heat profiles may also be designated, based upon the initial tissue thicknesses prior to joining tissues 120, 126.

In some examples, as illustrated in FIG. 10B, proximal heating element 234 is embedded in conductive proximal passive heat spreader 270, which is a component of proximal heating assembly 256 for tissue compression. In the example shown in FIG. 10B, proximal active heating element 234 has a serpentine shape to increase the surface area in contact with proximal heat spreader 270 to provide more effective heat transfer to sandwiched tissues 120, 126 to promote controlled desiccation and adhesion without cutting through the tissues too rapidly.

Figure 10C:
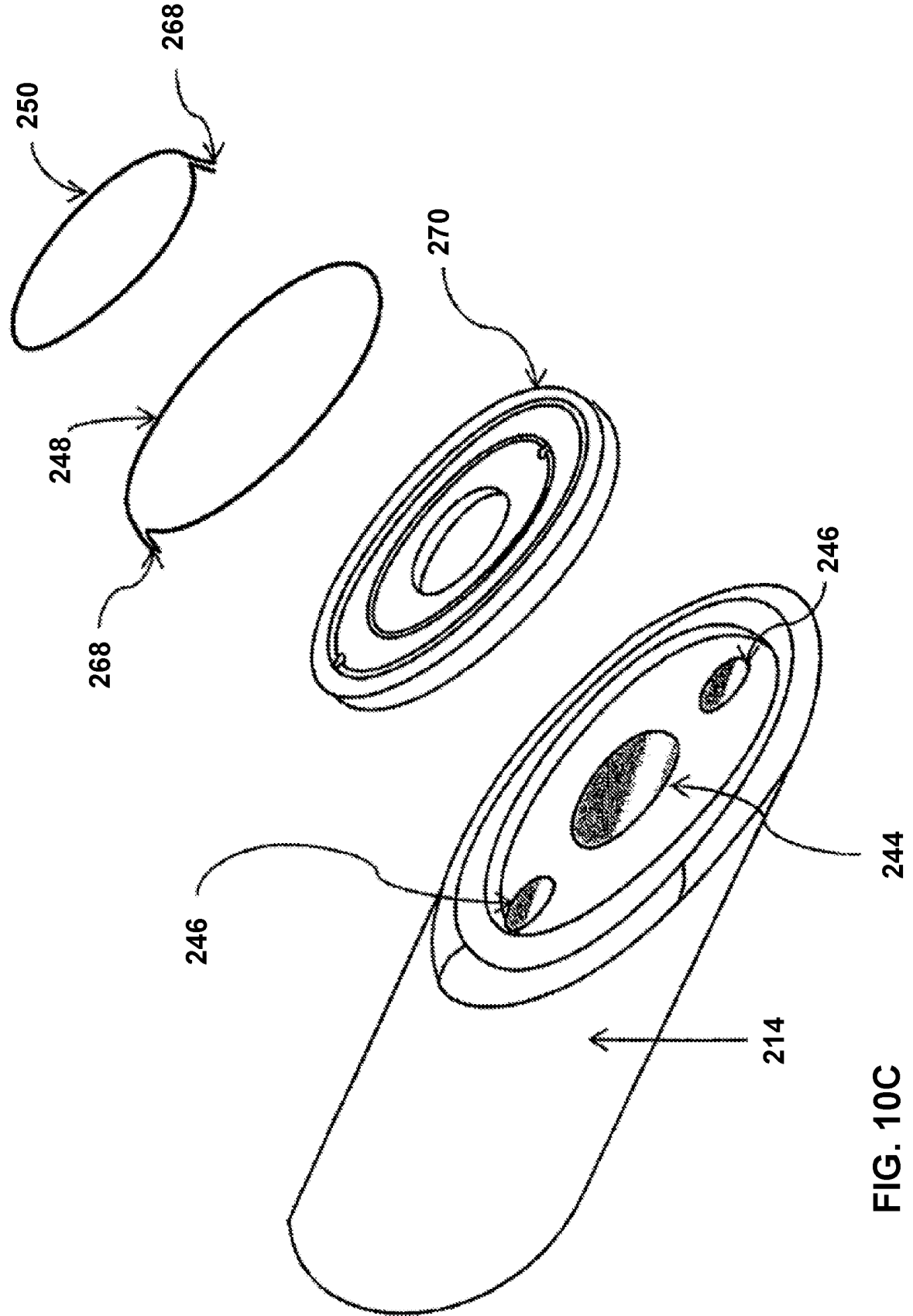
FIG. 10C is an exploded isometric view of the heating element of FIG. 10A.

In another example, as illustrated in FIG. 10C, proximal active heating element 234 within proximal heating assembly 256 may be configured to have separate elliptical elements 248, 250, that provide independent power delivery for heating and cutting. For instance, an outer element 248 can be configured to deliver reduced heat to promote controlled desiccation and adhesion in weld zone 278 without cutting through the tissue, while an inner element 250 can be configured to deliver increased heat to promote rapid cutting through the tissue in cutting zone 138.

Figures 17A, 17B:
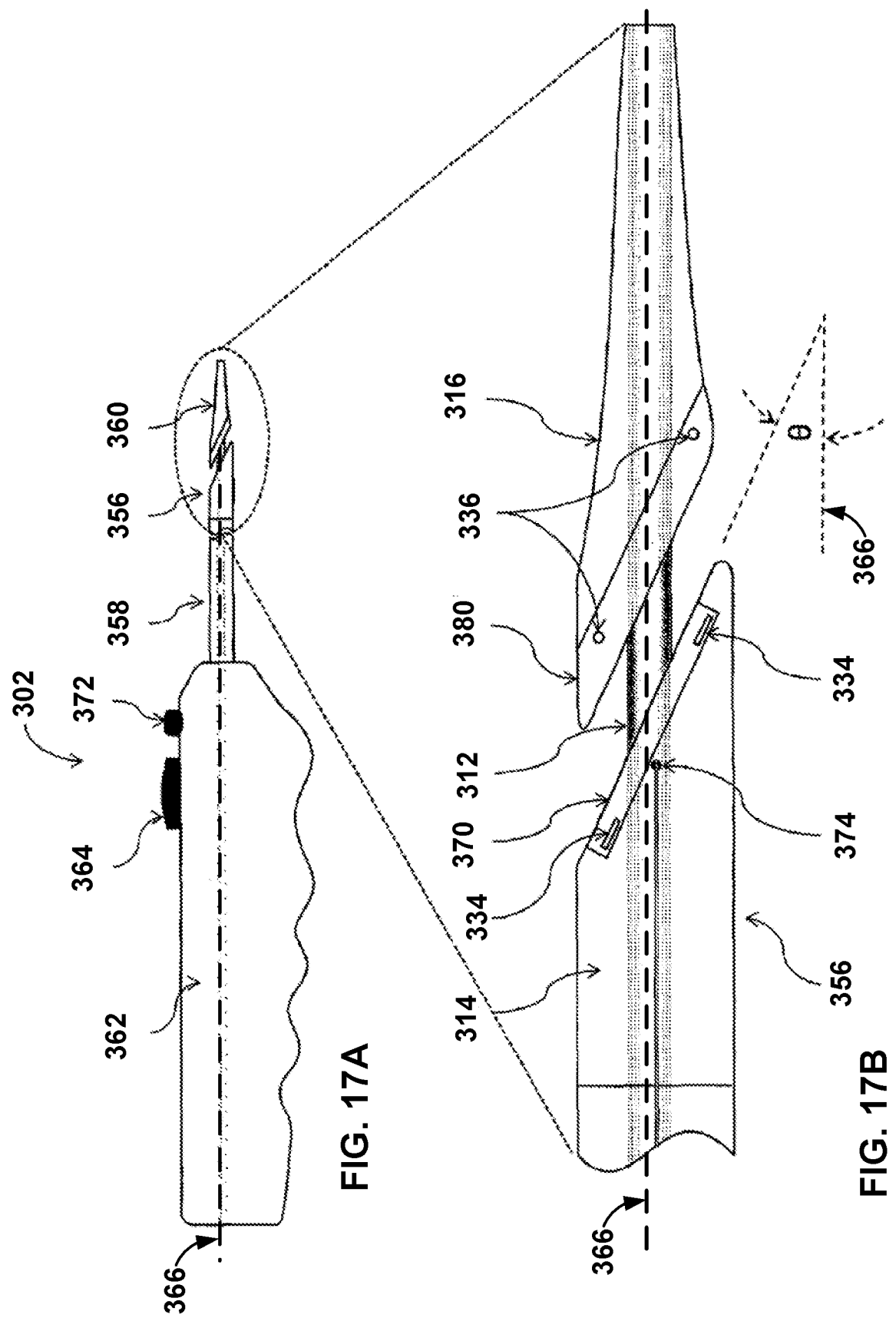
FIG. 17A is an elevational view of another example ablation device of the medical system of FIG. 1.
FIG. 17B is an elevational enlarged view of a portion of the ablation device of FIG. 17A.

FIGS. 17A and 17B illustrate another example ablation device 302, which is an example of ablation devices 102, 202 of FIGS. 1 and 7A-8B, respectively, except for the differences noted herein. Similar to ablation device 102 of FIG. 1, but unlike ablation device 202 of FIGS. 7A-8B, ablation device 302 of FIGS. 17A and 17B includes a distal active heating element 336 (e.g., distal active heating element 136 of FIG. 1). In the example shown in FIGS. 17A and 17B, distal active heating element 336 is embedded in a distal passive heat spreader 380 (e.g., distal passive heat spreader 280 of ablation device 202). Ablation device 302, including both an active proximal heating element 334 and an active distal heating element 336, may be beneficial in cases in which separate heating profiles are required for different tissue types. For example, when joining coronary sinus wall 120 to left atrium wall 126, it may be beneficial to apply more heat to left atrium wall 126 because left atrium wall 126 may dissipate more heat and requires more energy to denature the tissue.

Distal active heating element 336 may be constructed similarly to proximal active heating element 334 (e.g., proximal active heating elements 134, 234) within proximal heating assembly 356 (e.g., proximal heating assembly 256). In some examples, control circuitry 172 may also provide a closed-loop control of RF energy to distal active heating element 336, e.g., based on a signal generated by a temperature sensor and indicative of a temperature of or near heating element 336. This control of distal active heating element 336 may be independent of the control of proximal active heating element 334.

Additionally or alternatively, distal active heating element 336 can be heated using electrodynamic inductive energy. For instance, a primary coil can be integrated into proximal heating assembly 356, and a secondary coil, which can be tuned to the same natural frequency, can be embedded in distal heating assembly 360 (e.g., distal heating assembly 260 of FIGS. 7A-8B). As proximal heating assembly 356 heats, electrical current passes through the primary coil, creating a magnetic field which acts on the embedded coil in distal heating assembly 360, creating a current that heats the resistive element.

In some examples, the respective proximal and distal heating assemblies 356, 360 include non-stick surfaces to help prevent denatured tissue from bonding to ablation device 302. If tissue bonds to ablation device 302, then annular weld 278 between tissues 120, 126 can be weakened during removal of ablation device 302. One or more different coatings or surface modifications can be applied to the components to create a non-stick surface. In one example, components of ablation device 302 have a surface finish defining an average roughness (Ra) of less than about 16 Ra, coated using a high-temperature parylene. Other non-stick coatings, such as polytetrafluoroethylene (PTFE), titanium nitride (TiN), chromium Nitride (CrN), Dicronite, silicone, or other similar coatings may be used to prevent tissue adherence.

Some example techniques for using ablation device(s) 102, 202, 302 are as follows, with particular reference to FIGS. 1, 2, 15 and 16. A clinician selects an appropriate access site, such as the right jugular vein of a patient. The clinician introduces puncturing tool 108 (FIG. 1) into coronary sinus 122 and actuates a puncturing element, such as electrifiable distal tip 154 of puncturing tool 108, to pierce tissue walls 120, 126 and extend into left atrium 128. Once penetration from coronary sinus 122 to left atrium 128 has been achieved, the clinician positions a dilation element 110 in the newly formed punctures 162 and expands dilation element 110 radially outward (e.g., inflated) to dilate tissue punctures 162 to larger diameters (e.g., into dilated punctures 162), or to at least loosen the surrounding tissue for subsequent penetration by ablation device 102. Dilation element 110 can be coupled to puncturing tool 108, ablation device 202, or a distinct device.

The clinician advances guidewire 104 until guidewire 104 is positioned in the blood flow path of coronary sinus 122 sufficiently to allow puncturing tool 108 to be removed while retaining the position of guidewire 104 in left atrium 128.

Once guidewire 104 is sufficiently in position, as previously described, the clinician withdraws puncturing tool 108 completely from the patient's body, thus leaving guidewire 104 in the desired position and crossing from coronary sinus 122 to left atrium 128.

Guidewire 104 creates an access path for ablation device 202. Ablation device 202 is inserted into the patient by loading a proximal end of guidewire 104 into lumen 276 of distal body 216 of ablation device 202. Ablation device 202 is advanced further into the patient, tracking over guidewire 104, until tapered distal body 216 comes into contact with the selected shunt site (e.g., with target treatment site 150). Ablation device 202 can be tracked over guidewire 104 with distal body 216 extended (as shown in FIG. 8A) or retracted (as shown in FIG. 8B). Distal heating assembly 260 is extended and further advanced into left atrium 128 by advancing elongated structure 212 distally, thereby further dilating punctures 162 in the tissues, so that distal body 216 is positioned in left atrium 128, and proximal body 214 is in coronary sinus 122, with its proximal passive heat spreader surface 270 contacting inner wall 120 of the coronary sinus 122. At this juncture, dilated punctures 162 formed in adjoined walls 120, 126 of coronary sinus 122 and left atrium 128 may have recovered back to a smaller diameter and fit tightly around ablation device 202.

After distal body 216 is advanced into left atrium 128, as illustrated in FIG. 15, a slight tension, or alternatively a slight pressure, is applied to proximal passive heat spreader 270 to seat proximal passive heat spreader 270 against coronary sinus wall 120 and to promote tissue apposition. A blunt (e.g., rounded and flattened) shape of a proximal-most edge or end 252 of distal body 216 prevents distal body 216 from inadvertently retracting back through left atrium wall 126. Distal body 216 is then retracted to close the spacing between proximal and distal heating assemblies 256, 260, until walls 120, 126 of coronary sinus 122 and left atrium 128, respectively, are captured between proximal-facing and distal-facing surfaces 218, 224 of each of proximal heat spreader 270 and distal heat spreader 280, respectively.

A controlled tension is maintained between distal body 216 and proximal body 214, and at this juncture, with tissues 120, 126 securely clamped, energy is applied to proximal active heating element 234 (or to proximal active heating element 334 and distal heating element 336, in the case of modified example device 302 of FIGS. 17A and 17B). As active heating elements 234, 334, 336 weld and cut the tissues of coronary sinus wall 120 and left atrium wall 122, the proximal and distal heating assemblies will move closer to one another. When fully retracted, system 100 is designed so that the proximal and distal heating assemblies come into direct contact with one another to ensure a complete cut and capture of the tissue to be removed.

A variety of DC resistive energy profiles may be used to achieve the desired coaptation and cutting. For example, a rapidly stepped or ramped increase to achieve and maintain a desired temperature setting of about 150° C. to about 350° C. may be applied to maximize welding prior to cutting. Energy may be modulated based upon the impedance of the tissue or temperature feedback. Different energy-application durations or cyclic pulses may be used to enhance welding and cutting, while reducing heat transfer to adjacent tissues. Distal body 216 is configured to have insulating properties to reduce heat transfer to adjacent tissues and/or fluids. Active heating elements 234, 334, 336 are generally oval or elliptical shapes and cut a shunt 138 larger than the cross-sectional diameter of proximal body 214 (e.g., the cross-section taken perpendicular to longitudinal axis 266). Within each of the oval shapes of active cutting elements 234, 334, 336, there may be provided, if desired, a cavity 290 for capturing the tissues that have been cut. As noted above, the entire surfaces of proximal and distal heat assemblies 256, 260 may include non-stick coatings, such as PTFE, to discourage tissue adhesion.

Regarding the tissue-welding process, the applied DC resistive energy fuses or welds coronary sinus wall 120 and left atrium wall 126 together around perimeter 278 of shunt 138, creating an elongate aperture through opposing walls 120, 126 of coronary sinus 122 and left atrium 128, as well as through any intervening tissue. As formed, the elongate aperture may resemble a narrow slit. However, as pressurized fluid flow begins to occur through shunt 138, which creates a communicating aperture between coronary sinus 122 and left atrium 128, shunt 138 widens in response to the pressure, taking the shape of an ellipse as it opens to form a shunt of the desired size. This effect is illustrated in FIG. 16. The edges of shunt 138 are cauterized, forming an ovular weld band 278. Outward from weld band 278 is a coaptation (or "transition") area 298. As shown, cut area 138 corresponds to the shape of heating and/or cutting element(s) 134, 136, 234, 334, 336 of corresponding ablation device 102, 202, 302. Shunt aperture 138 can be of multiple shapes, such as round, oval, a slit, or a combination thereof. Tissue area 278 immediately surrounding cut 138 has been ablated and welded, due to proximal passive heating surface 270 being marginally smaller than distal-facing surface 218 in which proximal passive heating surface 270 is embedded. The heat from proximal passive heating surface 270 is also preferably spread over this area by a conductive material that can be above, below, or within heating surface 270 or proximal body 214, advantageously forming a temperature gradient. Once shunt 138 has been fully formed, the entire system 100, including ablation device 102, 202 and guidewire 104 are withdrawn.

Other example systems and techniques are contemplated, but not explicitly described or shown herein. For example, in certain applications, it may be advantageous to provide an outer sheath surrounding proximal body 214 and tapered at the same angle. After the creation of shunt 138, the outer sheath may be advanced until it comes into contact with wall 120 of coronary sinus 122. With slight forward (e.g., distal) pressure on the outer sheath, proximal body 214 and distal body 216 are retracted into the outer sheath. The outer sheath provides support to surrounding tissue 120, and prevents weld area 278 from being damaged during the removal step. The outer sheath may be utilized in conjunction with any of the previously disclosed examples.

In some examples, after welding tissues 120, 126, distal heating assembly 260 may be advanced to longitudinally separate distal heating assembly 260 from proximal heating assembly 256. Prior to retracting distal heating assembly 260 through newly formed shunt 138, distal heating assembly 260 may be rotated by about 45 to about 180 degrees, such that the proximal taper (e.g., proximal-most edge 252 of proximal-facing surface 224) of distal heating assembly 260 is oriented to create a ramp when being retracted through shunt 138. That is, proximal-most edge 252 of proximal-facing surface 224 can be re-oriented toward the center of shunt aperture 138, e.g., away from the welded perimeter 278, such that proximal-edge more effectively proximally penetrates back through shunt aperture 138.

In some examples, distal body 216 can be retracted by keeping distal and proximal heating assemblies 260, 256, respectively, together, applying heat, and applying a proximal retraction force to ablation device 202. The applied heat will cause welded tissue 278 to expand radially outward and away from ablation device 202 as ablation device 202 is removed.

In some examples, an inductive activation energy may be supplied from outside the patient's body, wherein the inductive activation energy does not have a direct electrical connection to ablation device 202. An emitter may be placed in close proximity to desired shunt location 150, adjacent to distal body 216. The activation energy then travels through the patient's skin and surrounding tissue without effect, but creates heat through reactive elements in distal body 216.

In some examples, ablation device 202, with cylindrical shape, includes a stationary proximal body 214 with movable distal body 216, wherein the interface between proximal body 214 and distal body 216 defines a coplanar interface (e.g., between distal-facing and proximal-facing surfaces 218, 224), and further wherein angle θ of the interface relative to longitudinal axis 266 is about 15 degrees to about 50 degrees.

In some examples, distal body 216 is radially expandable and collapsible to allow for a reduced-cross-sectional-area profile of distal body 216 for entry into and exit from left atrium 128, and an expanded-cross-sectional-area profile to increase the area of compression (e.g., of proximal-facing surface 224) for tissue welding and cutting. Distal body 216 can remain in the "closed," or reduced-area, profile configuration as ablation device 202 is advanced to target treatment site 150 for shunt 138, and distal body 216 enters left atrium 128, which limits potential tissue trauma as distal body 216 dilates through coronary sinus wall 120. Once ablation device 202 is in place at target site 150 for shunt 138, distal body 216 is retracted toward proximal body 214 and a compressive counter force from proximal body 214 is applied to rigid spreader face(s) 280 of distal body 216, which cause them to pivot to the "open," or expanded-area, profile configuration and apply a greater surface area of compression to adjacent tissues 120, 126 captured between proximal and distal bodies 214, 216.

Similarly, in some examples, distal body 216 is expandable to allow for a reduced-area profile of distal body 216 for entry into and exit from left atrium 128, and an expanded-area profile to increase the area of compression for tissue welding and cutting. For instance, distal body 216 may be composed of a flexible elastomeric material such as silicone, though other materials may be used. In a manner similar to the previous example, ablation device 202 may be positioned at target site 150 for shunt 138 while in the reduced-area-profile configuration, and distal body 216 is retracted proximally toward proximal body 214 and a compressive counter force from proximal body 214 is applied to the elastomeric material of distal body 216, which causes distal body 216 to expand radially outward and apply a greater surface area of compression to adjacent tissues 120, 126 captured between proximal and distal bodies 214, 216. As described above, this flexible elastomeric material can further enable distal body 216 to bend to perform the approximately 90-degree turn when maneuvering from the inner lumen of the delivery sheath 106 (FIG. 1) and outward through side opening 146 toward the target treatment site.

An approach for cooling proximal heating assembly 256 near proximal active heat element 234 may be desired to prevent unintended heat transfer to, and necrosis of, adjacent tissue. To achieve this, it is desired to keep the surface temperature of the components of ablation device 202 near proximal active and passive heat elements 234, 270 below about 150 Fahrenheit (65 Celsius). An example is contemplated wherein an inner infusion lumen, which may be or may include central lumen 244 and/or auxiliary lumens 246 of FIGS. 10A-11, is employed in proximal heating assembly 256 that allows room-temperature sterile saline to be infused through inner lumen(s) 244, 246, which exits proximal heating assembly 256 near proximal active heat element 234. In this example, the exit of auxiliary lumen(s) 246 is within about 2 mm of proximal active heat element 234, though the position can be up to about 10 mm spaced from proximal active heat element 234. In one particular method, the saline flow rate is between about 2 cc/min and about 5 cc/min, such as about 3 cc/min.

In some examples, an outer infusion sheath is employed that allows room-temperature sterile saline to be infused through the annular lumen defined between the exterior surface of proximal heating assembly 256 and the interior surface of the outer sheath. The saline may exit the annular outer lumen near proximal active heat element 234 on proximal body 214. The outer infusion sheath can include the vascular-access (e.g., delivery) sheath 106 of FIG. 1, or in other examples, an outer saline-infusion lumen can be incorporated separately. Like the previous example, the distal exit from the saline-infusion lumen is within about 10 mm from proximal active heat element 234, such as within about 2 mm of proximal active heat element 234. In such examples, the saline flow rate may between about 2 cc/min and about 5 cc/min, such as about 3 cc/min.

In some examples, a passive thermal-conductive element, which is embedded in proximal heating assembly 256, provides a heat sink to draw excess heat away from proximal active heat element 234 and the (e.g., plastic) material of proximal heating assembly 256, conducting the heat proximally through ablation device 202. The passive thermal-conductive element can be fabricated from aluminum, copper, stainless steel, ceramics and/or any other suitable thermally conductive materials.

Accordingly, although example systems and techniques have been shown and described, it is to be understood that all the terms used herein are descriptive rather than limiting, and that many changes, modifications, and substitutions may be made by one having ordinary skill in the art without departing from the spirit and scope of the invention. The following examples are examples of systems, devices, and methods described herein.

Example 1: In some examples, a method includes: creating a puncture through a coronary sinus wall of a coronary sinus of a patient and a left atrium wall of a left atrium of a heart of the patient; expanding a dilation element within the puncture to dilate the puncture, resulting in a dilated puncture; advancing a distal body of an ablation device through the dilated puncture and into the left atrium, wherein the ablation device comprises: an elongated structure; a proximal body coupled to the elongated structure, the proximal body defining a distal-facing surface configured to contact the coronary sinus wall surrounding the dilated puncture; the distal body coupled to the elongated structure, wherein the proximal body and the distal body are longitudinally translatable relative to each other, the distal body defining a proximal-facing surface positioned opposite the distal-facing surface and configured to contact the left atrium wall surrounding the dilated puncture; a first heating element disposed on the distal-facing surface; and a second heating element disposed on the proximal-facing surface. The method further includes axially translating at least one of the proximal body or the distal body to compress the coronary sinus wall and the left atrium wall between the first heating element and the second heating element; and actuating the first and second heating elements to ablate the tissue to create a shunt between the left atrium and the coronary sinus.

Example 2: In some examples of the method of example 1, each of the distal-facing surface and the proximal-facing surface of the ablation device forms an elliptical shape.

Example 3: In some examples of the method of example 1 or example 2, creating the puncture comprises advancing a puncturing tool through the coronary sinus wall and the left atrium wall, wherein the puncturing tool is physically distinct from the ablation device, and wherein the puncturing tool comprises the dilation element.

Example 4: In some examples of the method of example 3, creating the puncture further comprises delivering electrical energy to the coronary sinus wall and the left atrium wall via an electrifiable distal tip of the puncturing tool.

Example 5: In some examples of the method of example 4, the electrifiable distal tip of the puncturing tool comprises a plasma electrode.

Example 6: In some examples of the method of any of examples 3 through 5, the elongated structure of the ablation device defines a device inner lumen configured to receive the puncturing tool.

Example 7: In some examples of the method of any of examples 1 through 6, expanding the dilation element within the puncture comprises inflating a balloon to expand the puncture.

Example 8: In some examples of the method of example 7, the inflatable balloon, when inflated, defines an hourglass shape configured to inhibit axial translation of the balloon, the hourglass shape comprising a proximal inflatable portion configured to inflate within the coronary sinus and a distal inflatable portion configured to inflate within the left atrium.

Example 9: In some examples of the method of any of examples 1 through 8, further comprising expanding a positioning element of a delivery sheath to position a side opening of the delivery sheath against the coronary sinus wall, wherein the delivery sheath is configured to receive the ablation device.

Example 10: In some examples of the method of example 9, expanding the positioning element comprises inflating a balloon positioned circumferentially opposite the side opening of the delivery sheath.

Example 11: In some examples of the method of any of examples 1 through 10, the method further includes introducing a guidewire into vasculature of the patient through an entry point in a right internal jugular vein of the patient; and advancing the guidewire through the vasculature of the patient, wherein advancing the distal body of an ablation device through the dilated puncture comprises advancing the ablation device over the guidewire.

Example 12: In some examples of the method of any of examples 1 through 11, the proximal body of the ablation device defines a cross-sectional diameter of about 13 French (Fr) to about 21 Fr.

Example 13: In some examples of the method of any of examples 1 through 12, the distal body of the ablation device includes an atraumatic distal portion and the puncturing element comprising a distal puncture wire extending distally from the atraumatic distal portion.

Example 14: In some examples of the method of any of examples 1 through 13, axially translating the at least one of the proximal body or the distal body of the ablation device comprises actuating a proximal actuator of the ablation device to longitudinally translate the distal body.

Example 15: In some examples of the method of any of examples 1 through 14, the method further includes: advancing a guidewire through vasculature of the patient toward the coronary sinus wall; advancing a delivery sheath over the guidewire; introducing the puncturing element through an inner lumen of the delivery sheath and through a side opening defined by a side wall of the delivery sheath; and advancing the puncturing element distally out of the inner lumen of the delivery sheath to form the puncture through the coronary sinus wall and the left atrium wall.

Example 16: In some examples, a medical system includes: an ablation device configured to create a shunt between a left atrium of a heart of a patient and a coronary sinus of the patient, the ablation device includes an elongated structure; a proximal body coupled to the elongated structure, the proximal body defining a distal-facing surface configured to contact a coronary sinus wall of the coronary sinus; a distal body coupled to the elongated structure and longitudinally translatable relative to the proximal body, the distal body defining a proximal-facing surface positioned opposite the distal-facing surface and configured to contact a left atrium wall of the left atrium; a first heating element disposed on the distal-facing surface; and a second heating element disposed on the proximal-facing surface, wherein the first and second heating elements are configured to ablate tissue between the left atrium and the coronary sinus of the patient to create the shunt; and a dilation element configured to expand to dilate a puncture formed through the coronary sinus wall and the left atrium wall to facilitate introduction of the distal body of the ablation device into the left atrium.

Example 17: In some examples of the medical system of example 16, the elongated structure defines a longitudinal axis, and wherein each of the distal-facing surface of the proximal body and the proximal-facing surface of the distal body is oriented at an oblique angle relative to the longitudinal axis.

Example 18: In some examples of the medical system of example 16 or example 17, each of the distal-facing surface of the proximal body and the proximal-facing surface of the distal body forms an elliptical shape.

Example 19: In some examples of the medical system of any of examples 16 through 18, the medical system further includes a puncturing tool configured to form the puncture through the coronary sinus wall and the left atrium wall, wherein the puncturing tool comprises the dilation element.

Example 20: In some examples of the medical system of example 19, the puncturing tool further comprises an electrifiable distal tip.

Example 21: In some examples of the medical system of example 20, the electrifiable distal tip comprises a plasma electrode.

Example 22: In some examples of the medical system of any of examples 19 through 21, the elongated structure of the ablation device defines a central lumen configured to receive the puncturing tool.

Example 23: In some examples of the medical system of any of examples 16 through 22, the dilation element comprises an inflatable balloon.

Example 24: In some examples of the medical system of example 23, the inflatable balloon is configured to expand to an expanded configuration in which the inflatable balloon defines an hourglass shape, the hourglass shape comprising a proximal inflatable portion configured to inflate within the coronary sinus and a distal inflatable portion configured to inflate within the left atrium.

Example 25: In some examples of the medical system of any of examples 16 through 24, the medical system further includes an elongated delivery sheath defining a sheath inner lumen configured to receive the ablation device and facilitate advancement of the ablation device toward a target treatment site on the coronary sinus wall.

Example 26: In some examples of the medical system of example 25, a side wall of the delivery sheath defines a side opening through which the ablation device is configured to extend to engage with a target treatment site on the coronary sinus wall.

Example 27: In some examples of the medical system of example 26, the delivery sheath comprises a positioning element configured to position the side opening of the delivery sheath proximate the target treatment site on the coronary sinus wall.

Example 28: In some examples of the medical system of example 27, the positioning element of the delivery sheath comprises an inflatable balloon positioned circumferentially opposite from the side opening, the inflatable balloon configured to expand within the vasculature of the patient to position the side opening proximate the target treatment site.

Example 29: In some examples of the medical system of any of examples 16 through 28, the proximal body of the ablation device defines a cross-sectional diameter of about 13 French (Fr) to about 21 Fr.

Example 30: In some examples of the medical system of any of examples 16 through 29, the distal body of the ablation device comprises an atraumatic distal portion and a distal puncture wire extending distally from the atraumatic distal portion.

Example 31: In some examples of the medical system of example 30, the distal puncture wire comprises a Nitinol wire.

Example 32: In some examples of the medical system of any of examples 16 through 31, the ablation device further comprises a proximal actuator configured to longitudinally translate the distal body relative to the proximal body.

Example 33: In some examples of the medical system of any of examples 16 through 32, wherein the distal body of the ablation device is configured to deflect away from a longitudinal axis of the elongated structure in order to extend through the coronary sinus wall and the left atrium wall.

Example 34: In some examples, medical system includes: an ablation device configured to create a shunt between a first anatomical structure and a second anatomical structure of a patient, the ablation device includes an elongated structure; a proximal body coupled to the elongated structure, the proximal body defining a distal-facing surface configured to contact a first wall of the first anatomical structure; a distal body coupled to the elongated structure and longitudinally translatable relative to the proximal body, the distal body defining a proximal-facing surface positioned opposite the distal-facing surface and configured to contact a second wall of the second anatomical structure; a first heating element disposed on the distal-facing surface; and a second heating element disposed on the proximal-facing surface, wherein the first and second heating elements are configured to ablate tissues of the first wall and the second wall to create the shunt; a puncturing tool configured to form a puncture through the first and second walls; and an expandable balloon configured to expand to dilate the puncture to facilitate introduction of the distal body of the ablation device into the second anatomical structure.

Example 35: In some examples of the system of example 34, the system further includes a radiofrequency (RF) generator configured to deliver RF energy to the first and second heating elements.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical system comprising:
an ablation device configured to create a shunt between a left atrium of a heart of a patient and a coronary sinus of the patient, the ablation device comprising:
an elongated structure;
a proximal body coupled to the elongated structure, the proximal body defining a distal-facing surface configured to contact a coronary sinus wall of the coronary sinus;
a distal body coupled to the elongated structure and longitudinally translatable relative to the proximal body along the elongated structure, the distal body defining a proximal-facing surface positioned oppo-site the distal-facing surface and configured to contact a left atrium wall of the left atrium;
a first heating element disposed on the distal-facing surface of the proximal body; and
a second heating element disposed on the proximal-facing surface of the distal body, wherein the first and second heating elements are configured to ablate tissue between the left atrium and the coronary sinus of the patient to create the shunt; and
a dilation element configured to expand to dilate a puncture formed through the coronary sinus wall and the left atrium wall to facilitate introduction of the distal body of the ablation device into the left atrium.

2. The medical system of claim 1, wherein the elongated structure defines a longitudinal axis, and wherein each of the distal-facing surface of the proximal body and the proximal-facing surface of the distal body is oriented at an oblique angle relative to the longitudinal axis.

3. The medical system of claim 1, wherein each of the distal-facing surface of the proximal body and the proximal-facing surface of the distal body forms an elliptical shape.

4. The medical system of claim 1, further comprising a puncturing tool configured to form the puncture through the coronary sinus wall and the left atrium wall, wherein the puncturing tool comprises the dilation element.

5. The medical system of claim 4, wherein the puncturing tool further comprises an electrifiable distal tip.

6. The medical system of claim 1, wherein the dilation element comprises an inflatable balloon configured to expand to an expanded configuration in which the inflatable balloon defines an hourglass shape, the hourglass shape comprising a proximal inflatable portion configured to inflate within the coronary sinus and a distal inflatable portion configured to inflate within the left atrium.

7. The medical system of claim 1, wherein the distal body of the ablation device comprises an atraumatic distal portion and a distal puncture wire extending distally from the atraumatic distal portion.

8. The medical system of claim 1, wherein the ablation device further comprises a proximal actuator configured to longitudinally translate the distal body relative to the proximal body.

9. The medical system of claim 1, wherein the distal body of the ablation device is configured to deflect away from a longitudinal axis of the elongated structure in order to extend through the coronary sinus wall and the left atrium wall.

10. The medical system of claim 1, further comprising an elongated delivery sheath defining a sheath inner lumen configured to receive the ablation device and facilitate advancement of the ablation device toward a target treatment site on the coronary sinus wall.

11. The medical system of claim 10, wherein a side wall of the delivery sheath defines a side opening through which the ablation device is configured to extend to engage with a target treatment site on the coronary sinus wall.

12. The medical system of claim 11, wherein the delivery sheath comprises a positioning element configured to position the side opening proximate the target treatment site on the coronary sinus wall.

13. The medical system of claim 12, wherein the positioning element comprises an inflatable balloon positioned circumferentially opposite from the side opening, the inflatable balloon configured to expand within the vasculature of the patient to position the side opening proximate the target treatment site.

27

28

14. A medical system comprising:

an ablation device configured to create a shunt between a first anatomical structure and a second anatomical structure of a patient, the ablation device comprising:

an elongated structure;

a proximal body coupled to the elongated structure, the proximal body defining a distal-facing surface configured to contact a first wall of the first anatomical structure;

a distal body coupled to the elongated structure and longitudinally translatable relative to the proximal body along the elongated structure, the distal body defining a proximal-facing surface positioned opposite the distal-facing surface and configured to contact a second wall of the second anatomical structure;

a first heating element disposed on the distal-facing surface of the proximal body; and a second heating element disposed on the proximal-facing surface of the distal body, wherein the first and second heating elements are configured to ablate tissues of the first wall and the second wall to create the shunt;

a puncturing tool configured to form a puncture through the first and second walls; and an inflatable balloon configured to expand to dilate the puncture to facilitate introduction of the distal body of the ablation device into the second anatomical structure.

15. The system of claim 14, further comprising a radiofrequency (RF) generator configured to deliver RF energy to the first and second heating elements.

16. A method comprising:

creating a puncture through a coronary sinus wall of a coronary sinus of a patient and a left atrium wall of a left atrium of a heart of the patient;

expanding a dilation element within the puncture to dilate the puncture, resulting in a dilated puncture;

advancing a distal body of an ablation device through the dilated puncture and into the left atrium, wherein the ablation device comprises:

an elongated structure;

a proximal body coupled to the elongated structure, the proximal body defining a distal-facing surface configured to contact the coronary sinus wall surrounding the dilated puncture;

the distal body coupled to the elongated structure, wherein the proximal body and the distal body are longitudinally translatable relative to each other along the elongated structure, the distal body defining a proximal-facing surface positioned opposite the distal-facing surface and configured to contact the left atrium wall surrounding the dilated puncture;

a first heating element disposed on the distal-facing surface of the proximal body; and a second heating element disposed on the proximal-facing surface of the distal body;

axially translating at least one of the proximal body or the distal body to compress the coronary sinus wall and the left atrium wall between the first heating element and the second heating element; and actuating the first and second heating elements to ablate the tissue to create a shunt between the left atrium and the coronary sinus.

17. The method of claim 16, wherein each of the distal-facing surface and the proximal-facing surface of the ablation device forms an elliptical shape.

18. The method of claim 16, wherein expanding the dilation element within the puncture comprises inflating a balloon to expand the puncture, wherein, when inflated, the inflatable balloon defines an hourglass shape configured to inhibit axial translation of the balloon, the hourglass shape comprising a proximal inflatable portion configured to inflate within the coronary sinus and a distal inflatable portion configured to inflate within the left atrium.

19. The method of claim 16, further comprising:

introducing a guidewire into vasculature of the patient through an entry point in a right internal jugular vein of the patient; and advancing the guidewire through the vasculature of the patient, wherein advancing the distal body of the ablation device through the dilated puncture comprises advancing the ablation device over the guidewire.

20. The method of claim 16, wherein the distal body of the ablation device comprises an atraumatic distal portion and a distal puncture wire extending distally from the atraumatic distal portion.

21. The method of claim 16, wherein axially translating the at least one of the proximal body or the distal body of the ablation device comprises actuating a proximal actuator of the ablation device to longitudinally translate the distal body.

22. The method of claim 16, further comprising:

advancing a guidewire through vasculature of the patient toward the coronary sinus wall;

advancing a delivery sheath over the guidewire;

introducing a puncturing element through an inner lumen of the delivery sheath and through a side opening defined by a side wall of the delivery sheath; and advancing the puncturing element distally out of the inner lumen of the delivery sheath to create the puncture through the coronary sinus wall and the left atrium wall.

23. The method of claim 16, wherein creating the puncture comprises advancing a puncturing tool through the coronary sinus wall and the left atrium wall, wherein the puncturing tool is physically distinct from the ablation device, and wherein the puncturing tool comprises the dilation element.

24. The method of claim 23, wherein creating the puncture further comprises delivering electrical energy to the coronary sinus wall and the left atrium wall via an electrifiable distal tip of the puncturing tool.

25. The method of claim 16, further comprising expanding a positioning element of a delivery sheath to position a side opening of the delivery sheath against the coronary sinus wall, wherein the delivery sheath is configured to receive the ablation device.

26. The method of claim 25, wherein expanding the positioning element comprises inflating a balloon positioned circumferentially opposite the side opening of the delivery sheath.

* * * * *